US011103525B2

(12) United States Patent
Svenningsson et al.

(10) Patent No.: US 11,103,525 B2
(45) Date of Patent: Aug. 31, 2021

(54) IDOXURIDINE AND ITS ANALOGS AS NEUROPROTECTANS FOR THE TREATMENT OF PARKINSONISM

(71) Applicants: Per Svenningsson, Stockholm (SE); Lina Leinartaite, Vilnius (LT); Magdalena Otrocka, Gnesta (SE); Vedran Hasimbegovic, Handen (SE); Birgitta Pettersson, Hagersten (SE)

(72) Inventors: Per Svenningsson, Stockholm (SE); Lina Leinartaite, Vilnius (LT); Magdalena Otrocka, Gnesta (SE); Vedran Hasimbegovic, Handen (SE); Birgitta Pettersson, Hagersten (SE)

( * ) Notice: Subject to any disclaimer, the term of this patent is extended or adjusted under 35 U.S.C. 154(b) by 0 days.

(21) Appl. No.: 16/478,721

(22) PCT Filed: Feb. 6, 2018

(86) PCT No.: PCT/SE2018/050107
§ 371 (c)(1),
(2) Date: Jul. 17, 2019

(87) PCT Pub. No.: WO2018/143893
PCT Pub. Date: Aug. 9, 2018

(65) Prior Publication Data
US 2019/0388451 A1    Dec. 26, 2019

(30) Foreign Application Priority Data

Feb. 6, 2017   (SE) .................................... 1750096-8

(51) Int. Cl.
*A01N 43/04*      (2006.01)
*A61K 31/70*      (2006.01)
*A61K 31/7072*    (2006.01)

(52) U.S. Cl.
CPC ............................... *A61K 31/7072* (2013.01)

(58) Field of Classification Search
None
See application file for complete search history.

(56) References Cited

U.S. PATENT DOCUMENTS 4,895,937 A * 1/1990 Bardos .................. C07H 19/06
                                                      536/28.1
5,962,459 A   10/1999 Piazza et al.

FOREIGN PATENT DOCUMENTS

CN         106220669         12/2016

OTHER PUBLICATIONS

Elbaz et al. Journal of Clinical Epidemiology (2002), vol. 55, pp. 25-31.*
Ascherio et al. Lancet Neurol (2016), vol. 15, pp. 1257-1272.*
Jolleys JV. Treatment of shingles and post-herpetic neuralgia. BMJ. 1989;298(6687):1537-1538. doi:10.1136/bmj.298.6687.1537.*
Lilie et al. Drugs Aging (2003), vol. 20 (8), pp. 561-570.*
Albanese, "Diagnostic criteria for Parkinson's disease," Neurol. Sci. 24(Suppl. 1):s23-6, May 2003.
Chon et al., "Targeting nuclear thymidylate biosynthesis," Mol. Aspects Med., 53:48-56, Feb. 2017.
Dunham et al., "GPR37 surface expression enhancement via N-terminal truncation or protein-protein interactions," Biochemistry, 48(43):10286-97, Oct. 2009.
Dusonchet et al., "Targeted overpression of the parkin substrate Pael-R in the nigrostriatal system of adult rats to model Parkinson's disease," Neurobiol. Dis., 35(1):32-41, Jul. 2009.
Freskos, "Synthesis of 2'-Deoxypyrimidine Nucleosides via Copper (I) Iodide Catalysis," Nucleosides Nuleotides,8(4):549-55, Oct. 1989.
Gandia et al., "The Parkinson's diesease-associated GPR37 receptor-mediated cytotoxicity is controlled by its intracellular cysteine-rich domain," J. Neurochem., 125(3):362-72, May 2013.
Imai et al.. "An unfolded putative transmembrane polypeptide, which can lead to endoplasmic reticulum stress, is a substrate of Parkin," Cell, 105(7):891-902, Jun. 2001.
Kinsella et al., "Preclinical toxicity and efficacy study of a 14-day schedule of oral 5-iodo-2pyrimidinone-2'-deoxyribose as a prodruc for 5-iodo-2'-deocyuridine radiosetisitixation in U251 human glioblastoma xenografts," Clin. Cancer Res., 6(4):1468-75, Apr. 2000.
Kubota et al., "Suppressive effects of 4-phenylbutyrate on the aggregation of Pael receptors and endoplasmic reticulum stress," J. Neurochem., 97(5):1259-68, Jun. 2006.
Lundius et al., "Functional GPR37 trafficking protects against toxicity induced by 6-OHDA, MPP+ or rotenone in a catecholaminergic cell line," J. Neurochem., 124(3):410-7, Feb. 2013.
Lundius et al., "GPCRs Regulating Catecholaminergic Cell Survival and Function—Focus on GPR37," Thesis for Dept. of Clin. Neurosci., Karolinska Institutetet, Stockholm Sweden,78 pages Dec. 2013.
Lundius et al., "GPR37 Trafficiking to the Plasma Membrane Regulated by Prosaposin and GM1 Gangliosides Promotes Cell Viability" J. Biol. Chem., 289(8):4660-73, Dec. 2013.
Marazziti et al., "Induction of macroautophagy by overexpression of the Parkinson's disease-associated GPR37 receptor," FASEB J., 23(6):1978-87, Feb. 2009.
Meyer et al., "GPR37 and GPR37L1 are receptors for the nuroprotective and glioprotective factors prosaptide and prosaposin," Proc. Natl. Acad. Sci. USA., 110(23):9529-34, Jun. 2013.

(Continued)

*Primary Examiner* — Patrick T Lewis
(74) *Attorney, Agent, or Firm* — Fish & Richardson P.C.

(57) ABSTRACT

The invention relates to compounds that are useful in the treatment of parkinsonism, such as parkinsonism in connection with Parkinson's disease (PD); dementia with Lewy bodies (DLB); multiple system atrophy (MSA); corticobasal degeneration (CBD); or progressive supranuclear palsy (PSP). The said compounds include in particular idoxuridine and analogs thereof as well as their metabolic precursors, such as ropidoxuridine. The invention further relates to method for identifying compounds useful for the treatment of parkinsonism, said methods comprising detecting the capability of compound to increase the amount of GPR37 in cell membranes. The invention further relates to methods for the chemical synthesis of ropidoxuridine.

17 Claims, 14 Drawing Sheets

(56) References Cited

OTHER PUBLICATIONS

Murakami et al., "Pael-R is accumulated in Lewy bpdoes of Parkinson's disease," Ann. Neurol., 55(3):439-42, Mar. 2004.
PCT International Preliminary Report on Patentability in Appln. No. PCT/SE2018/050107, dated Mar. 7, 2019, 21 pages.
PCT International Search Report and Written Opinion in Appln. No. PCT/SE2018/050107, dated Apr. 11, 2018, 21 pages.
Rautio et al., "Prodrugs: design and clinical applications," Nat. Rev. Drug Discov., 7(3):255-70, Mar. 2008.
Rezgaoui et al., "The neuropeptide head activator is a high-affinity ligand for the orphan G-protein-coupled receptor GBPR37," J.Cell Sci., 119(3):542-9, 2006.
Robas et al, "Macimizing serendipity: strategies for identigying ligands for orphan G-Protein-coupled receptors," Curr. Opin. Pharmacol., 3(2):121-6, Apr. 2003.
Rolland et al., "Convenient Preparation of 2-Deoxy-3,5-di-O-p-Toluoyl-a-D-erythro-pentofuranosyl Chloride," Synth. Commun., 27(20):3505-11, Mar. 1997.
Saif et al., "IPdR: a novel oral radiosensitizer," Expert Opin. Investig. Drugs, 16(9):1415-24, Aug. 2007.
Sakib et al., "The significance of G-protein-coupled receptor crystallography for drug discovery," Pharmacol. Rev., 63(4):901-37, Dec. 2011.
Schulz-Schaeffer, "Is Cell Death Primary or Secondary in the Pathophysiology of Idiopathic Parkinson's disease?" Biomolecules 5(3):1467-79, Jul. 2015.
Schure et al., "Improved Stereoselective Synthesis of the β-Anomer of 1-[3,5-Bis-O-(p-chlrobenzoyl)-2-deoxy-D-ribofuranosyl]-5-iodo-2-pyrimidinone," Org. Process Res. Dev., 3(2):135-8, Jan. 1999.
Van der Brug et al., "Prkinson's disease: From human genetics to clinical trials," Sci. Transl. Med., 7(305):305ps20, Sep. 2015.
Wang and Takahashi, "Expanding insights on the involvement of endoplasmic reticulum stress in Parkinson's disease," Antioxid. Redox Signal, 9(5):553-61,Apr. 2007.
Wang et al., "REG4 promotes peritoneal metastasis of gastric cancer through GPR37," Oncotarget, 7(19):27874-88, May 2016.
Zhang et al., "Parkin functions as an E2-dependent ubiquitin-protein ligases and promotes the degradation of the synaptic vesicle-associated protein, CDCrel-1," Proc. Natl. Acad. Sci. USA., 97(24):13354-9, Nov. 2000.

* cited by examiner

Murakami, T. et al. (2004) *Annals of neurology* 55, 439-442

□ N2a-wild type ■ N2a-GPR37-tGFP

A

B

A

B

*Reagents and conditions:* (a) Ag$_2$SO$_4$, I$_2$, MeOH (94%) (b) HMDS, TMS-Cl quant. yield (c) For 4a, R=Cl: SnCl$_4$ DCM gives alpha anomer 4a (58.7%) For 4b, R=Me: CHCl$_3$, gives beta anomer 4b (CuI catalyzed: 31%, Metal free 19%) (d) NH$_3$/MeOH (alpha anomer 1a: 62%) (beta anomer 1b: 41,7%)

Nucleoside:

2'-Deoxynucleoside:

IDOXURIDINE AND ITS ANALOGS AS NEUROPROTECTANS FOR THE TREATMENT OF PARKINSONISM

CROSS-REFERENCE TO RELATED APPLICATIONS

This application is a National Stage application under 35 U.S.C. § 371 of International Patent Application No. PCT/SE2018/050107, filed Feb. 6, 2018, which claims priority to Sweden Application Serial No. 1750096-8, filed Feb. 6, 2017, all of which are herein incorporated by reference in their entireties.

TECHNICAL FIELD

The invention relates to compounds that are useful in the treatment of parkinsonism, such as parkinsonism in connection with Parkinson's disease (PD); dementia with Lewy bodies (DLB); multiple system atrophy (MSA); corticobasal degeneration (CBD); or progressive supranuclear palsy (PSP). The said compounds include in particular idoxuridine and analogs thereof as well as their metabolic precursors, such as ropidoxuridine. The invention further relates to method for identifying compounds useful for the treatment of parkinsonism, said methods comprising detecting the capability of compound to increase the amount of GPR37 in cell membranes. The invention further relates to methods for the chemical synthesis of ropidoxuridine.

BACKGROUND ART

Parkinson's disease (PD) is a common neurodegenerative disorder which mostly affects dopaminergic neurons in substantia nigra pars compacta and, to a lesser extent, several other brain regions (1). Progressive loss of dopaminergic neurons results in a number of symptoms including tremor, bradykinesia and rigidity. Today, there are several drugs used in the clinics which alleviate the main symptoms of PD. However, none of them can stop or halt progression of the disease and they have no impact on survival time (1). The reason is that current treatment strategies are focused on compensating for dopaminergic-cell loss by increasing dopamine levels, and thus, the underlying mechanism of neurodegeneration remains untouched. Since PD is an age-related disease, with aging population an increased prevalence is expected in the future which underscores the importance of discovery of novel treatment strategies.

Likewise, the incidence of the atypical forms of parkinsonism; dementia with Lewy bodies (DLB); multiple system atrophy (MSA); progressive supranuclear palsy (PSP); corticobasal degeneration (CBD) are increasing with age. PD, DLB and MSA are disorders where accumulation of alpha-synuclein is pathognomonic. DLB is characterized by fluctuating dementia and hallucinations in addition to rigidity, bradykinesia, whereas MSA patients suffer from severe dysautonomia together with rigidity, bradykinesia. PSP and CBD are tauopathies with astrocytic accumulation of four repeat tau. PSP is characterized by impaired postural control and falls, vertical supranuclear gaze palsy and frontal disinhibition, whereas CBD patients suffer from corticosensory neglect, apraxia and speech problems. All atypical forms of parkinsonism respond poorly towards existing therapies.

On a subcellular level, PD and DLB is characterized by accumulation of intracellular eosinophilic/proteinaceous inclusions called Lewy bodies (LBs) (2), particularly in dopamine neurons. Whether LBs themselves are cytotoxic, coincidental or protective is still issue of debate (3). Nevertheless, it is generally accepted that protein misfolding and aggregation play an important role in PD progression. Among a good number of different proteins found in Lewy bodies, the membrane receptor GPR37 is one of the components constituting the core structure of it (4) (FIG. 1), suggesting that GPR37 might be involved in early pathological events preceding LB formation. In addition, GPR37 is a substrate of Parkin, a ubiquitin ligase, loss-of-function of which is responsible for autosomal recessive juvenile parkinsonism (AR-JP) and is associated with abnormal accumulation of insoluble GPR37 (5-7). Along this line, misfolding and aggregation of GPR37 is indicated to induce/be involved in PD pathology-associated cellular events such as ER stress, macroautophagy and cell death (7-10).

Intriguingly, the biological function of GPR37 seems to be neuroprotective. Although this protein is still considered orphan G-protein coupled receptor, three different macromolecules where suggested to transmit pro-survival signals via GPR37 (11-13). Moreover, it has been shown that increased levels of GPR37 at the plasma membrane protects cultured dopaminergic neuroblastoma cells from toxic effects of experimental parkinsonism-inducing drugs, namely 6-OHDA, MPP+ and rotenone, which stimulates oxidative stress (14) (FIG. 1). Taking into account that 30 to 50% of marketed drugs acts through GPCR's (15,16), GPR37 stands out as a prominent target for modulation of PD progression. As mentioned above, however, the drawback for GPR37 neuroprotective function is its intrinsic tendency to misfold and aggregate, which complicates its forward trafficking to the plasma membrane. In fact, GPR37 displays poor trafficking into plasma membrane upon transfection into most cell types (17).

The nucleoside analog idoxuridine (2'-deoxy-5-iodouridine) is known as an antiviral (anti-herpesvirus) drug. However, it is not previously disclosed that idoxuridine and its analogs are capable of increasing translocation of GPR37 to cell membranes. Further, it is not previously disclosed that idoxuridine has antiparkinsonism-related cytoprotective effect.

DISCLOSURE OF THE INVENTION

Figure 1A:
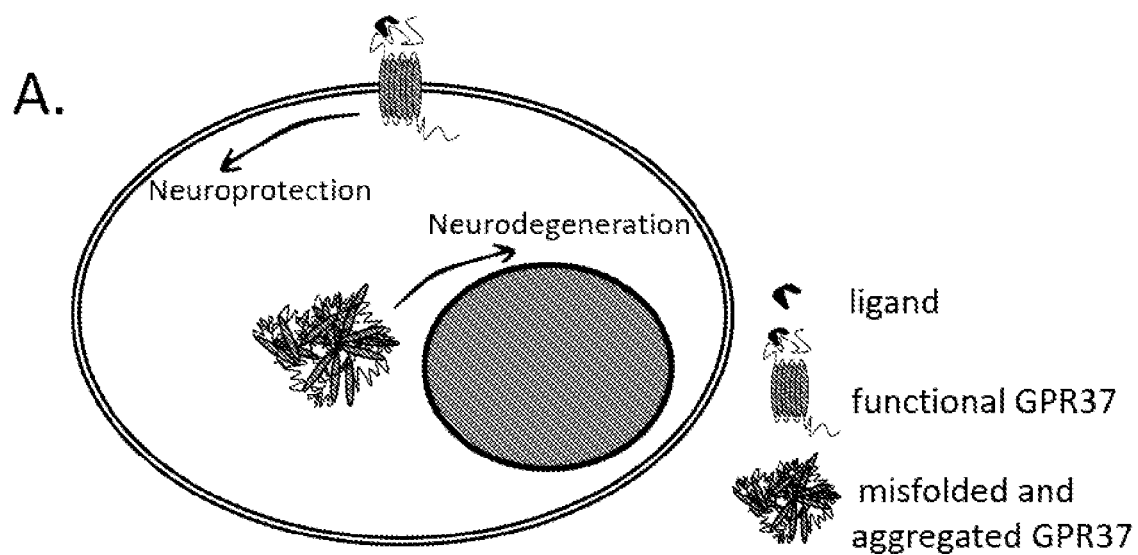
FIG. 1. GPR37 displays a neuroprotective function while in plasma membrane. A. Schematic representation of GPR37 function dependence on cellular localization. B. GPR37 is found in Lewy bodies and Lewy neurites in postmortem human brains from patients with PD or dementia with Lewy bodies (4). C. Differentiation of N2a cells to dopamine-like neurons (using serum starvation together with dbcAMP treatment) is accompanied by increased levels of GPR37-tGFP in the plasma membrane and protection from parkinsonian drug 6-OHDA (14) (undifferentiating media: DMEM+10% fetal bovine serum; differentiating media: OPTI-MEM+1% fetal bovine serum+1 mM dbcAMP).
Figure 1B:
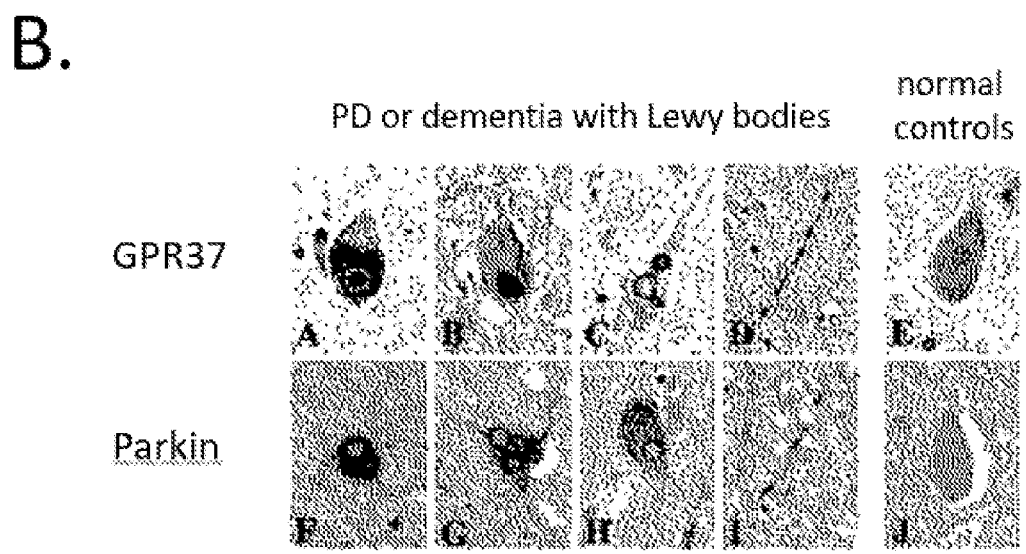

According to the invention, idoxuridine and analogs thereof have surprisingly been identified as cytoprotective agents, with a cellular action mechanism associated with increased level of GPR37 in the plasma membrane. Moreover, a metabolic precursor of idoxuridine, ropidoxuridine, which is efficiently converted to idoxuridine by a hepatic aldehyde oxidase, has been identified as a potential drug that can be administrated orally, is more stable and less toxic in vivo (18,19).

Consequently, in a first aspect the invention provides a compound for use against parkinsonism, said compound having the general formula (I) or (II):

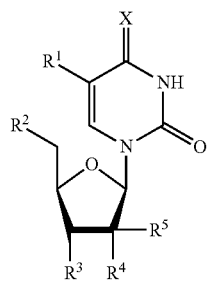

(I)

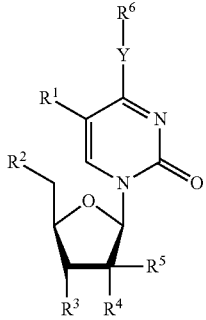

(II)

or a prodrug thereof, or a pharmaceutically acceptable salt or ester of said compound or prodrug, wherein $R^1$, $R^2$ and $R^3$ are independently (a) a halogen atom;
(b) a hydroxyl group;
(c) an amino group;
(d) a sulfhydryl group;
(e) a nitro group;
(f) an azido group;
(g) a cyano group;
(h) an ethenyl group;
(i) an ethynyl group;
(j) an aromatic/non-aromatic heterocyclic group;
(k) an aryl group,
  wherein hydrogen atoms in (h), (i), (j) and (k) are optionally substituted with halogen, hydroxyl, nitro, azido, cyano, amino, sulfhydryl, phenyl, ethenyl, ethynyl, or an aromatic/non-aromatic heterocyclic group, and wherein the hydrogen atoms in the said phenyl, ethenyl, ethynyl, or aromatic/non-aromatic heterocyclic group are optionally substituted with halogen, hydroxyl, nitro, azido, cyano, amino, or sulfhydryl;
(l) methyl substituted with halogen, hydroxyl, nitro, azido, cyano, amino, sulfhydryl, phenyl, ethenyl, ethynyl, or an aromatic/non-aromatic heterocyclic group, and wherein the hydrogen atoms in the said phenyl, ethenyl, ethynyl, and aromatic/non-aromatic heterocyclic group are optionally substituted with halogen, hydroxyl, nitro, azido, cyano, amino, or sulfhydryl; or
(m) oxygen substituted with $C_1$-$C_{20}$ alkyl, $C_1$-$C_{20}$ acyl, $C_1$-$C_{20}$ alkoxycarbonyl, or carbamoyl;

X is O or S;

Y is H, O, S, or N;

$R^4$ and $R^5$ is independently H, halogen, or $C_1$-$C_{20}$ alkyl; and $R^6$ is $C_1$-$C_{20}$ alkyl or $C_1$-$C_{20}$ acyl.

In a preferred aspect, the said compound has the general formula (III):

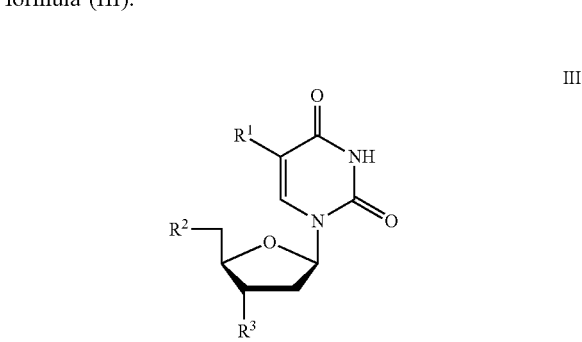

III or a prodrug thereof, or a pharmaceutically acceptable salt or ester of said compound or prodrug, wherein $R^1$, $R^2$ and $R^3$ are as defined in claim 1.

The compounds for use according to the invention may also be administered as prodrugs that may be converted to the active ingredient in question after metabolic transformation in vivo. The term "prodrug" means a pharmacologically acceptable derivative, such as an ester or an amide, which derivative is biotransformed in the body to form the active drug. Conventional procedures for the selection and preparation of suitable prodrug derivatives are described e.g. in (20, 21).

For compounds to be used according to the invention, suitable prodrugs include e.g. compounds lacking the deoxyribose moiety. It is known that nucleobases and analogs of nucleobases can be converted in vivo to nucleosides and nucleotides, as well as analogs of nucleosides and nucleotides, as described for fluorouracil e.g. in (22).

The term "halogen" shall mean fluorine, chlorine, bromine or iodine.

The term "aryl" refers to a hydrocarbon ring system having at least one aromatic ring. Examples of aryls are phenyl, pentalenyl, indenyl, indanyl, isoindolinyl, chromanyl, naphthyl, fluorenyl, anthryl, phenanthryl and pyrenyl.

Preferably, in the compounds having formula (III), $R^1$, $R^2$ and $R^3$ are independently chosen from a halogen atom, a hydroxyl group, an amino group, an optionally substituted ethynyl group, or an optionally substituted phenyl group, wherein the hydrogen atoms in the said ethynyl and phenyl can be substituted with a halogen atom, a hydroxyl group, or an amino group.

More preferably, $R^1$, $R^2$ and $R^3$ are independently chosen from a halogen atom, a hydroxyl group, an amino group, an ethynyl group, an aminophenyl group, a hydroxyphenyl group or a halophenyl group.

In another preferred form, $R^2$ and $R^3$ are hydroxyl groups, and the said compound has the formula IV, wherein $R^1$ is as defined above for formula I.

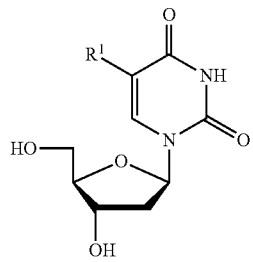

IV

Preferably, the compound having formula IV for use according to the invention is chosen from the group consisting of:

2'-deoxy-5-iodouridine (idoxuridine);

2'-deoxy-5-(3-aminophenyl)-uridine;

2'-deoxy-5-ethynyluridine; and

2'-deoxy-5-hydroxyuridine or a prodrug thereof, or a pharmaceutically acceptable salt or ester of said compound or prodrug.

More preferably, the compound for use according to the invention is deoxy-5-iodouridine (idoxuridine),

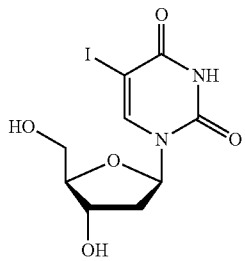 [SMILES: O=c1[nH]c(=O)n([C@H]2C[C@@H](O)[C@@H](CO)O2)cc1I]

or a prodrug thereof, or a pharmaceutically acceptable salt or ester of said compound or prodrug.

The said prodrug of idoxuridine is preferably 1-((2R,4S,5R)-4-hydroxy-5-(hydroxymethyl)tetrahydrofuran-2-yl)-5-iodopyrimidin-2(1H)-one (ropidoxuridine).

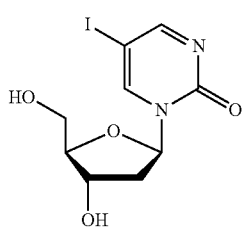 [SMILES: O=c1ncc(I)cn1[C@H]1C[C@@H](O)[C@@H](CO)O1]

Alternatively, said prodrug of idoxuridine is 4-amino-1-((2R,4S,5R)-4-hydroxy-5-(hydroxymethyl)tetrahydrofuran-2-yl)-5-iodopyrimidin-2(1H)-one (5-Iodo-2'-deoxycytidine).

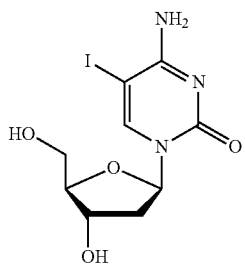 [SMILES: Nc1nc(=O)n([C@H]2C[C@@H](O)[C@@H](CO)O2)cc1I]

Additional preferred compounds of the invention are compounds having the general formula (V) or (VI):

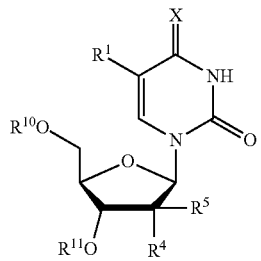

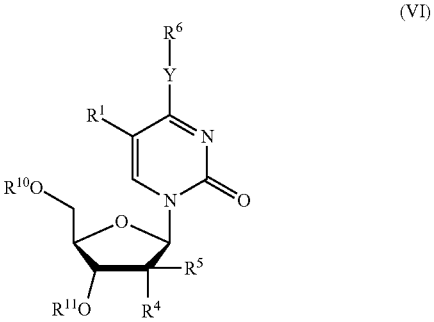

wherein X, Y, $R^4$, $R^5$ and $R^6$ are as defined in claim 1; and $R^{10}$ and $R^{11}$ are independently $C_1$-$C_{20}$ alkyl, $C_1$-$C_{20}$ acyl, $C_1$-$C_{20}$ alkoxycarbonyl, or carbamoyl.

The term "parkinsonism" means one or more medical conditions chosen from the group consisting of Parkinson's disease (PD); dementia with Lewy bodies (DLB); multiple system atrophy (MSA); corticobasal degeneration (CBD); and progressive supranuclear palsy (PSP).

A further aspect of the invention is a method for the treatment of parkinsonism, comprising administering to a patient in need of such treatment an effective amount of a compound as defined above.

Yet another aspect of the invention is a pharmaceutical composition for use in the treatment of parkinsonism, said composition comprising a compound as defined above as active ingredient, in combination with a pharmaceutically acceptable diluent or carrier.

Yet another aspect of the invention is a method (screening method) for identifying a compound that is useful in the treatment of parkinsonism, said method comprising the following steps:

(a) culturing eukaryotic cells, such as N2a cells, stably expressing GPR37;

(b) contacting the cells with a variety of candidate compounds;

(c) detecting the amount of GPR37 present in the cell membrane and/or in the endoplasmic reticulum of the said cells;

wherein an increased amount of GPR37 in the cell membrane is an indication of a candidate compound being useful in the treatment of parkinsonism.

Preferably, the said GPR37 is coupled to green fluorescent protein (tGFP) and the amount of GPR37 is detected by fluorescence.

Preferably, the said screening method comprises the additional step of comparing the capability of (i) the candidate compound to increase the amount of GPR37 in the cell membrane with (ii) the capability of idoxuridine to increase the amount of GPR37 in the cell membrane, wherein a similar or increased capability of the candidate compound to increase the amount of GPR37 in the cell membrane is an indication of a compound being useful in the treatment of parkinsonism.

In yet another aspect, the invention comprises a method for the treatment of parkinsonism, comprising administering to a patient in need of such treatment an effective amount of a compound identified by the screening method as defined above.

In a further aspect, the invention provides a method for the synthesis of ropidoxuridine, comprising the following steps:
(a) iodination of 2-hydroxy-pyrimidine hydrochloride, optionally performed in the presence a silver salt;
(b) silylation of (5-iodopyrimidin-2(1H)-one) using at least one silylating agent;
(c) glycosylation of 5-iodo-2-((trimethylsilyl)oxy)-pyrimidine with protected 2-deoxy-β-D-ribofuranose, optionally performed in the presence of a catalyst;
(d) quenching the reaction mixture of step (c) with an alcohol, and purifying the crude residue containing protected ropidoxuridine;
(e) deprotection procedure by any technique known in the art, including, but not limited to, treatment with methanol/sodium methoxide affording the beta anomer, ropidoxuridine.

The said monosilylated iodopyrimidine is preferably a compound of the formula (VII):

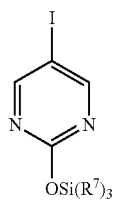

(VII)

wherein each R⁷ is an optionally substituted $C_1$-$C_{20}$ alkyl group independently selected from the group consisting of straight chain alkyl groups, branched alkyl groups, and cyclic alkyl groups.

The said catalyst in step (c) is preferably copper(I)iodide or trimethylsilyl trifluoromethanesulfonate (TMS-Triflate). The coupling process in step (c) is also possible to perform without any catalyst.

The said protected 1-halo-2-deoxy-β-D-ribofuranose is preferably a compound of the formula (VIII):

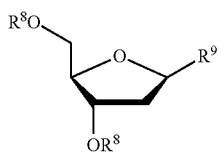

(VIII)

wherein each R⁸ is an optionally substituted $C_1$-$C_{20}$ acyl group, independently selected from the group consisting of straight chain acyl groups, branched acyl groups, and benzoyl groups; and wherein R⁹ is 1-halo, 1-alkoxy, 1-acyloxy (including acetoxy, benzoyloxy and substituted benzoyloxy).

Preferably, the said protected 1-halo-deoxyribofuranose or 1-acyl-deoxyribofuranose is selected from the group consisting of:

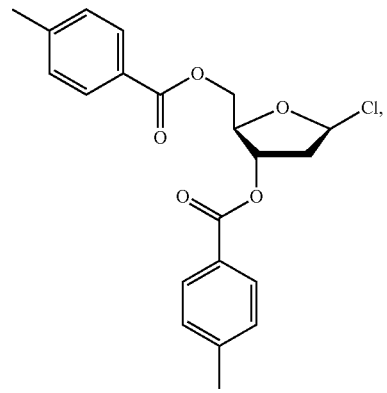

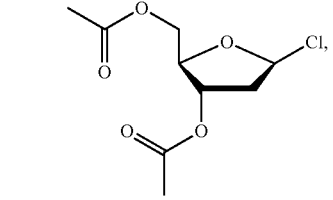

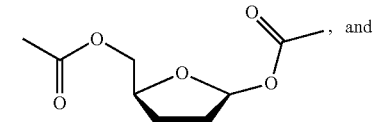

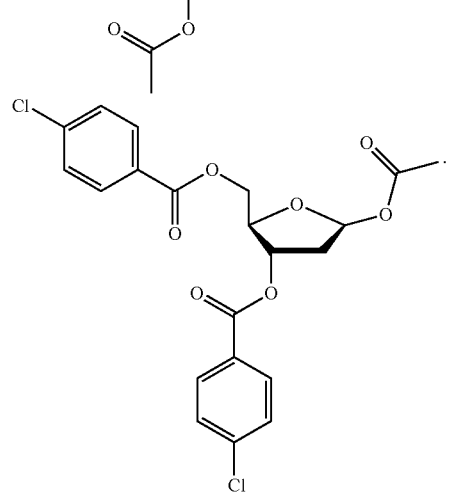

The said silylating reagent is a preferably a trimethylsilyl (TMS) reagent. More preferably, each silylating reagent is selected from the group consisting of hexamethyldisilizane (HMDS) and chlorotrimethylsilane (TMSCl). For instance, the silylating reagents can be HMDS and TMSCl in combination. Optionally, the said silylation reaction is carried out in the presence of ammonium sulfate.

The said quenching agent in step (d) is preferably methanol. The said solvent with low water solubility in step (c) is preferably chloroform or dichloromethane.

Step (e) preferably involves deprotecting the product of step (d) by adding sodium methoxide or potassium carbonate to a methanol or THF solution of protected ropidoxuridine obtained in step (d). Alternatively, step (e) involves deprotecting the product of step (d) by adding a solution of ammonia in methanol or alkylamine in methanol to protected ropidoxuridine obtained in step (d).

EXAMPLES OF THE INVENTION

Example 1: GPR37-tGFP Translocation Assay

Cell Culture:

N2a cells (also known as Neuro2a cells), a fast-growing mouse neuroblastoma cell line is commercially available from ATCC. N2a-GPR37-tGFP cells were generated as described in (14). The GPR37-tGFP construct was purchased from Origene (Rockville, Md., USA). tGFP (TurboGFP) is an improved variant of the green fluorescent protein CopGFP cloned from copepod *Pontellina plumata*. It possesses bright green fluorescence that is visible earlier than fluorescence of other green fluorescent proteins.

N2a-WT and N2a-GPR37-tGFP cells were cultured in Dulbecco's modified Eagle's medium (DMEM, high glucose, no pyruvate, no glutamine) supplemented with 10% heat inactivated fetal bovine serum (FBS), 200 µM L-glutamine, 100 U/mL penicillin and 100 µg/mL streptomycin at 37° C. and 5% $CO_2$. N2a-GPR37-tGFP cells were maintained with 50-250 µg/ml geneticin.

Cell Differentiation:

N2a-WT and N2a-GPR37-tGFP cells were differentiated in Dulbecco's modified Eagle's medium (DMEM, high glucose, no pyruvate, no glutamine) supplemented with 1% heat inactivated fetal bovine serum (FBS), 200 µM L-glutamine, penicillin 500 units/ml and streptomycin 0.5 mg/ml at 37° C. and 5% $CO_2$ for 72 h.

Figure 2:
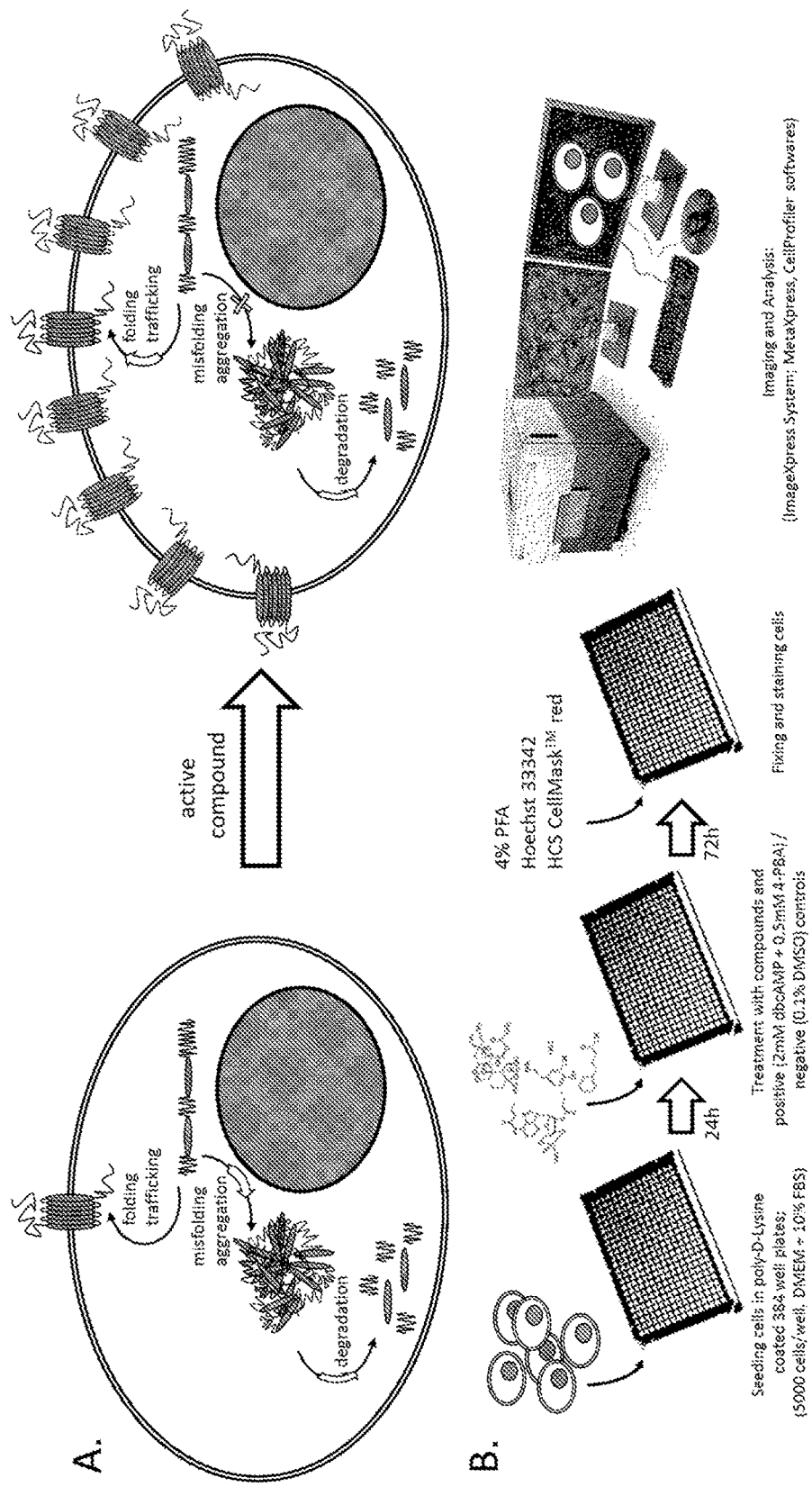
FIG. 2. Schematic representation of the rationale and the basic steps of GPR37-translocation assay. A. GPR37 is prone to misfolding and aggregation, which, in metabolically-active cells, are followed by degradation and results in low levels of functional receptor in the plasma membrane. The primary targets of the screening assay are compounds that can directly or indirectly facilitate maturation and trafficking of GPR37 to the plasma membrane. B. N2a cells stably expressing GPR37-tGFP are seeded in poly-D-Lysine coated 384 well plates at density 5000 cells/well. 24 h later cells are treated with compounds, including positive and negative controls, and incubated for 72 h. Then cells are fixed with 4% PFA and additionally stained with Hoechst 33342 (nuclei) and HCS CellMask™ red (cell body) to enable segmentation of the plasma membrane. Acquisition of fluorescence images is done using ImageXpress high content screening system (Molecular Devices). Quantification of GPR37-tGFP levels in the plasma membrane is done using CellProfiler software.

Assay Workflow (FIG. 2):

N2a cells stably expressing GPR37-tGFP were seeded in 384 BDFalcon BioCoat Poly-D-Lysine coated plates at a density of 5000 cells/well, and 50 µL incubation volume of maintenance medium. Cells were incubated at 37° C., 5% $CO_2$ using humidity chamber. 24 h later, the cells were treated with 10 µL of compounds of desired concentration, including positive (2 mM dibutyryl-cAMP+0.5 mM 4-phenylbutyrate) and negative controls (0.1% DMSO), and incubated for 72 h. Cells were fixed with 4% PFA by adding 20 µL of 16% PFA directly to cell medium, incubating for 20 min and washing with PBS-Tween20 (0.05%). Directly after fixation cells were stained for nuclei with Hoechst 33342 (0.01 mg/mL) and for cell bodies with HCS CellMask™ Red stain (Thermo Fisher Scientific Inc.) (0.001 mg/mL) by incubating with the dyes for 30 min in PBS-Tween20 (0.05%) followed by washing with PBS. All the additional steps, including cell seeding were performed using Multidrop Combi dispenser (Thermo Scientific) and washing steps were done by means of HydroSpeed™ plate washer (Tecan). The images were captured using ImageXpress Micro XLS Widefield High-Content Analysis System (Molecular Devices, LLC) in 3 fluorescent channels (ImageXpress filters are listed, followed by excitation/emission in nm): DAPI (387/447), FITC (482/536) and TexasRed (562/624). Binning 2 was applied during the acquisition and digital confocal option was used for FITC and TexasRed filters. Typically, 5 images were taken per well at magnification 20× and stored as 16 bit, gray scale tif files along with metadata in Oracle database, for further analysis.

Figure 3:
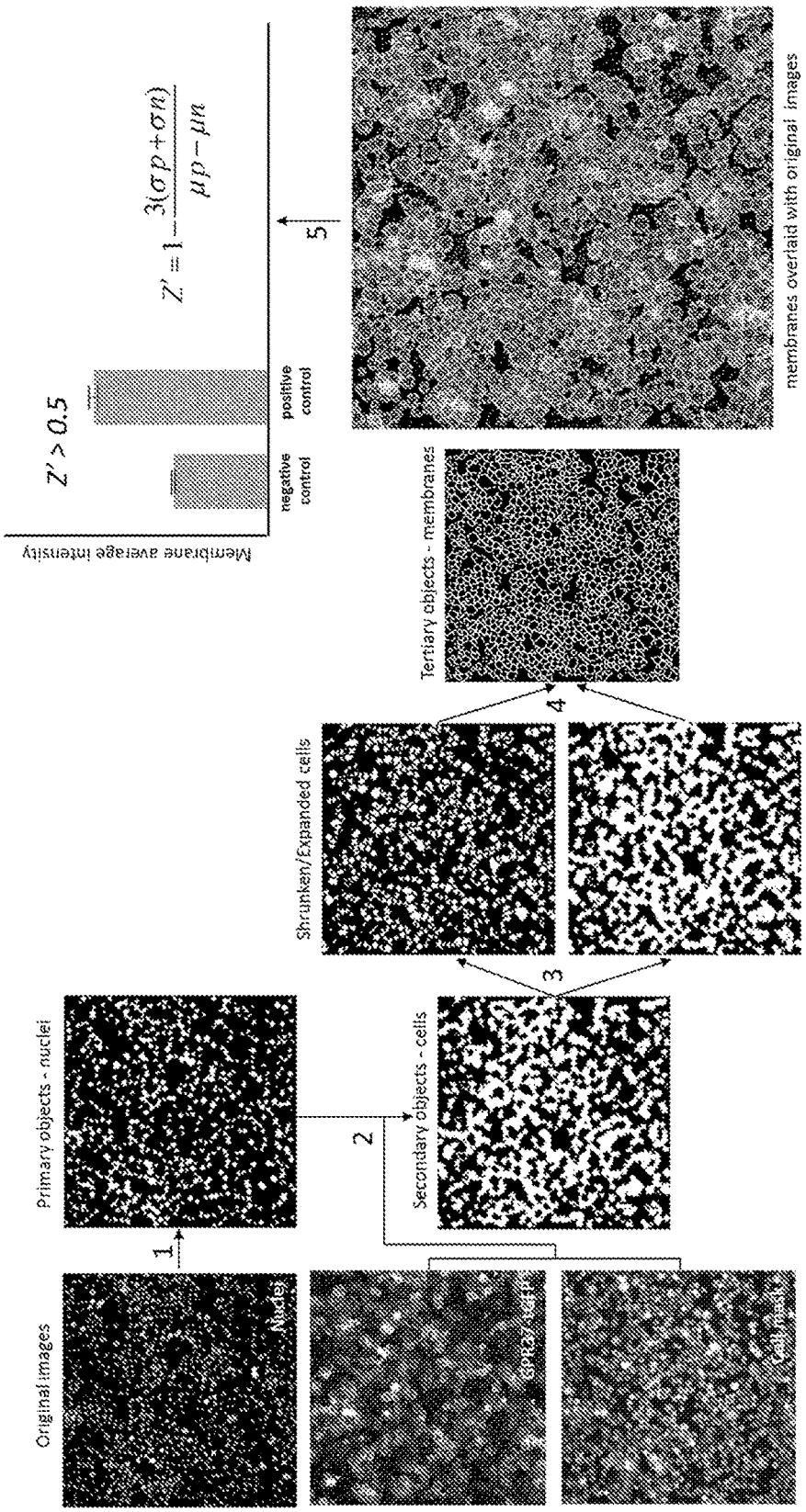
FIG. 3. Schematic representation of Image analysis pipeline and final outcome data. Segmentation of the plasma membrane is performed in five main steps: 1) identification of nuclei (primary objects) using nuclear stain, 2) determination of cell borders using primary objects as seeds and growing these objects in respect of tGFP and HCS CellMask™ fluorescence intensity (secondary objects), 3) shrinking and expending secondary objects, 4) subtraction of shrunken cells from expended cells which results in membrane segmentation (tertiary objects), 5) tGFP fluorescence intensity is calculated within tertiary objects. Z' factor is a quality measure of an assay which describes how well separated positive and negative controls are. Assays having Z' factors above 0.5 are considered good assays.

Image Analysis and Quantification of Plasma Membrane Level of GPR37-tGFP:

Quantification of GPR37-tGFP levels in the plasma membrane was done using CellProfiler™ software. CellProfiler™ is an open-source cell image analysis software available at www.cellprofiler.org. An image analysis pipeline used for membrane segmentation consisted of 5 main steps (FIG. 3): 1) segmentation of nuclei (primary objects); 2) segmentation of cell bodies (secondary objects); 3) shrinking and expending cell bodies; 4) subtraction of shrank cells from expanded cells (tertiary objects—membranes); 5) calculating tGFP fluorescence in the membranes. The outcome membrane fluorescence intensity was normalized by subtracting negative control from all the data and then setting positive control as 100% active. The automated analysis was followed by manual evaluation of identified active compounds.

Figure 1C:
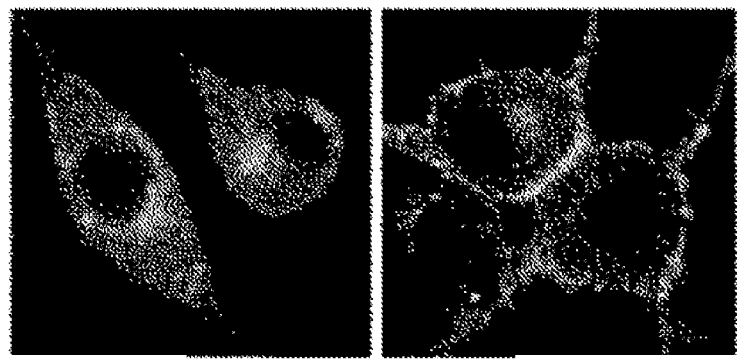
Figure 1C:
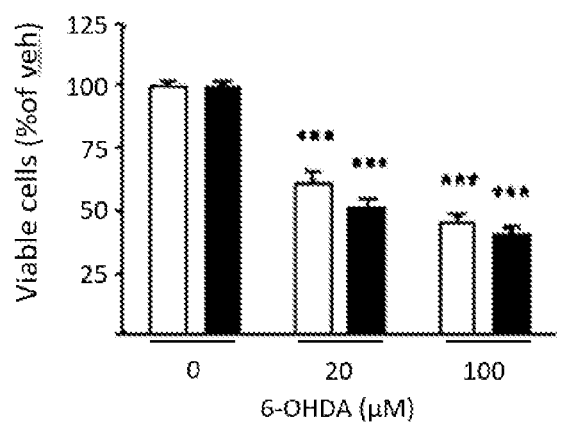
Figure 1C:
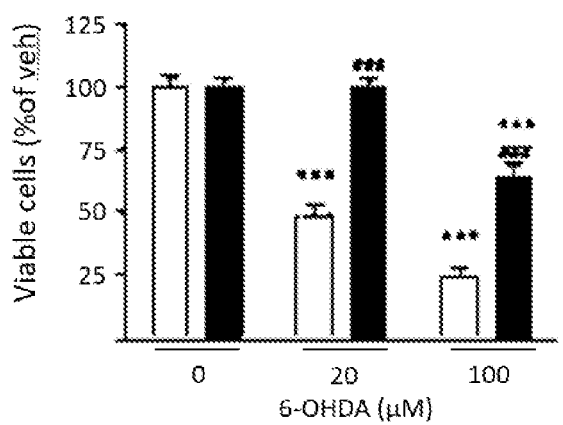

Results:

It has previously been shown that differentiation of N2a cells to dopaminergic neurons using serum starvation and dbcAMP treatment leads to increased levels of GPR37-tGFP in the plasma membrane (14) (FIG. 1C). It was now found that treatment with dibutyryl-cAMP without starvation also leads to remarkable increase of GPR37-tGFP in the plasma membrane with much smaller effect on cell proliferation (data not shown). Even greater increase of GPR37-tGFP in the plasma membrane is achieved using combination of dibutyryl-cAMP and 4-PBA, where the latter is suggested to display chemical chaperon function (23), thus serving as a valid positive control (FIG. 5C). In summary, the developed GPR37-translocation assay meets all the basic requirements needed to perform High Throughput Screening (HTS) in 384-well plate format as it consistently produce good Z' factor values (>0.5).

Example 2: Screening of Compound Library

Figure 4:
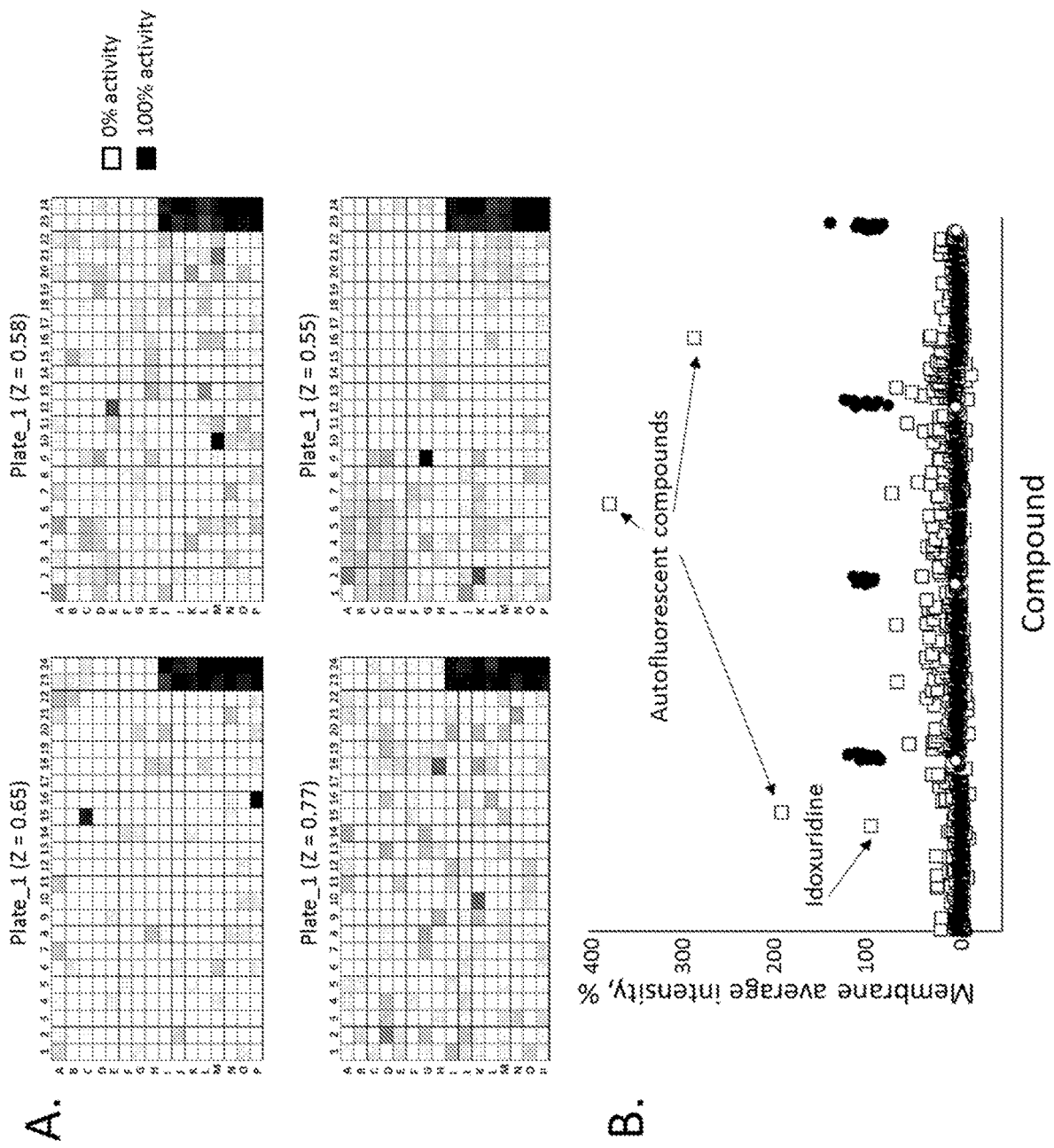
FIG. 4. Heat Maps and summary plot of the membrane average intensity for all Prestwick screened compounds. Membrane average intensity values obtained from image quantification are converted to % activation values based on the average negative (0% activation) and positive controls (100% activation) on each individual plate. A. Negative and positive controls are located in the last two columns of each plate (A-H and I-P rows respectively). Idoxuridine treated cells are in Plate_1 well C15, whereas other compounds that display high membrane average intensity turned out to be false-positives either due to being autofluorescent or due to dusts/"green" cell clumps/etc. in the wells. B. Open circles (○) represent the negative controls, closed circles (●) represent the positive controls and the squares (□) represent the compounds. The most outstanding outliers, with activity between 2 and 4 times higher that positive control, turned out to be autofluorescent.

Workflow:

Using the above described GPR37-tGFP translocation assay, a high-throughput screening (HTS) of a compound library was performed. The Prestwick Library® containing 1200 approved (FDA, EMA or other agencies) drugs was provided by the Chemical Biology Consortium Sweden (CBCS). For primary screening purpose the compound stock solutions at 10 mM in DMSO were replicated from Labcyte 1536 HighBase plates (LP-03730) to 384-well polypropylene plates (784201, Greiner) by transferring 120 nl solution by means of acoustic dispensing (Echo 550, Labcyte) to columns 1-22. Columns 23 and 24 were left empty for the controls. At the day of the experiment the compounds were diluted by adding 20 µl distillated water using a Multidrop Combi reagent dispenser (Thermo Scientific) and then 10 µl of intermediate solution were transferred to the cells using a Bravo liquid handling platform equipped with a 384-well head (Agilent). Thus using 10 µL treatment volume all compounds were subjected to cells at 10 µM concentration containing 0.1% DMSO (FIG. 4). Each tested plate contained 16 wells with cells treated with positive control and 16 wells with negative control. In the second step, 28 compounds selected from the prime screen were tested at three concentrations (2, 10, 20 µM; data not shown).

Figure 5:
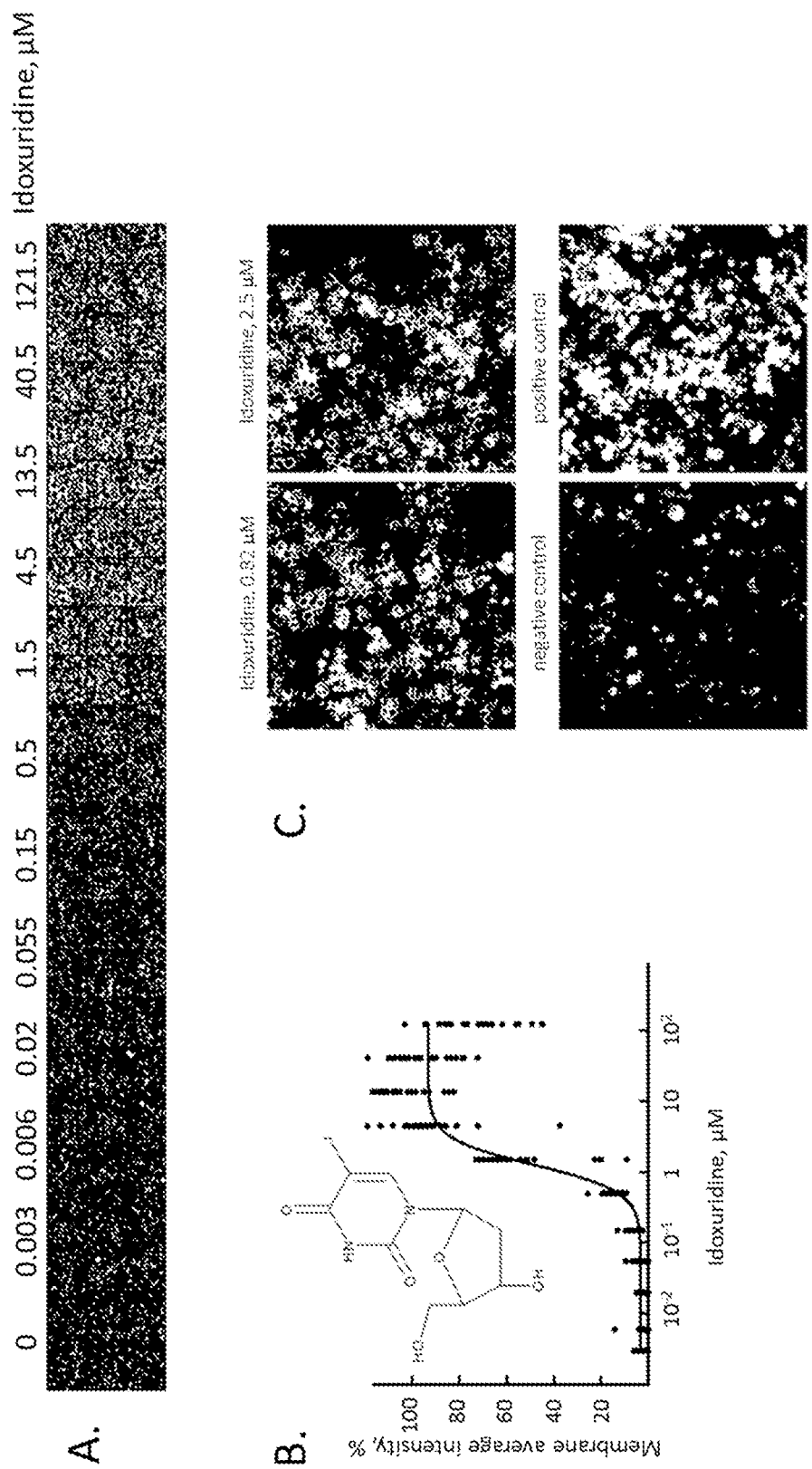
FIG. 5. Dose response of Idoxuridine on GPR37-tGFP translocation to the plasma membrane. A. Thumbnails of one out of five tGFP fluorescence images taken in each well that were treated with certain Idoxuridine concentration (indicated above the thumbnails). B. Idoxuridine structure and dose response curve where the levels of GPR37-tGFP in the plasma membrane are expressed as a percentage of positive control. C. Representative fluorescence images of idoxuridine treated cells in comparison to cells treated with positive and negative controls (both, Hoechst 33342 (nuclei) and GPR37-tGFP, fluorescence is shown in these images).

Results:

After filtering false-positives, mainly caused by autofluorescence, one compound, idoxuridine, showed up as a strong hit (about 100% activity of positive control) (FIG. 5). Dose response studies revealed that, in respect to treatment with idoxuridine, GPR37-tGFP level at the plasma membrane increase in a dose response manner up to around 5 µM of compound and display 50% activity of positive control at around 1 µM (FIG. 5), thus 2 µM concentration was chosen for future cytoprotective studies.

Example 3: Cytoprotective Effect of Idoxuridine (a) 6-OHDA
Workflow:
Test compound (5 µL) of desired concentration (Idoxuridine, final concentration 2 µM); positive control (dibutyryl-cAMP, final concentration 1 mM); and negative control (DMSO, final concentration 0.1%) were plated in a 96-well plate. Cells were seeded on top of compounds in differentiation medium at a density of 20,000 cells/well with a volume of 85 µL/well. The cells were incubated at +37° C., 5% $CO_2$ using humidity chamber for 72 h, then treated with increasing concentrations of the neurotoxic compound 6-hydroxydopamine (6-OHDA; treatment volume 10 µL; 6-OHDA stock solutions contains 0.07% of ascorbic acid).

After 24 hours, an MTT assay was performed. The MTT assay is a colorimetric assay wherein NAD(P)H-dependent cellular oxidoreductase enzymes reflect the number of viable cells present. These enzymes reduce the tetrazolium dye 3-(4,5-dimethylthiazol-2-yl)-2,5-diphenyltetrazolium bromide (MTT) to its insoluble formazan, which has a purple color.

MTT (0.5 mg/mL) was added to the medium and the cells were incubated for 2.5 h at 37° C., 5% $CO_2$. The cells were lysed, and formazan product was dissolved by adding one volume (100 µL) of 10% SDS containing 0.01 M HCl solution directly to the medium and incubating in dark over the night. Absorbance was measured at 570 nm (formazan product) and at 650 nm (reference) using a Tecan Spark® 10M microplate reader. Data was normalized by first subtracting 100 µM 6-OHDA treated cell data from the rest and then setting 6-OHDA-untreated cell data of each compound-treatment as 100% viable. Data from three independent experiments were pooled together.

Figure 6:
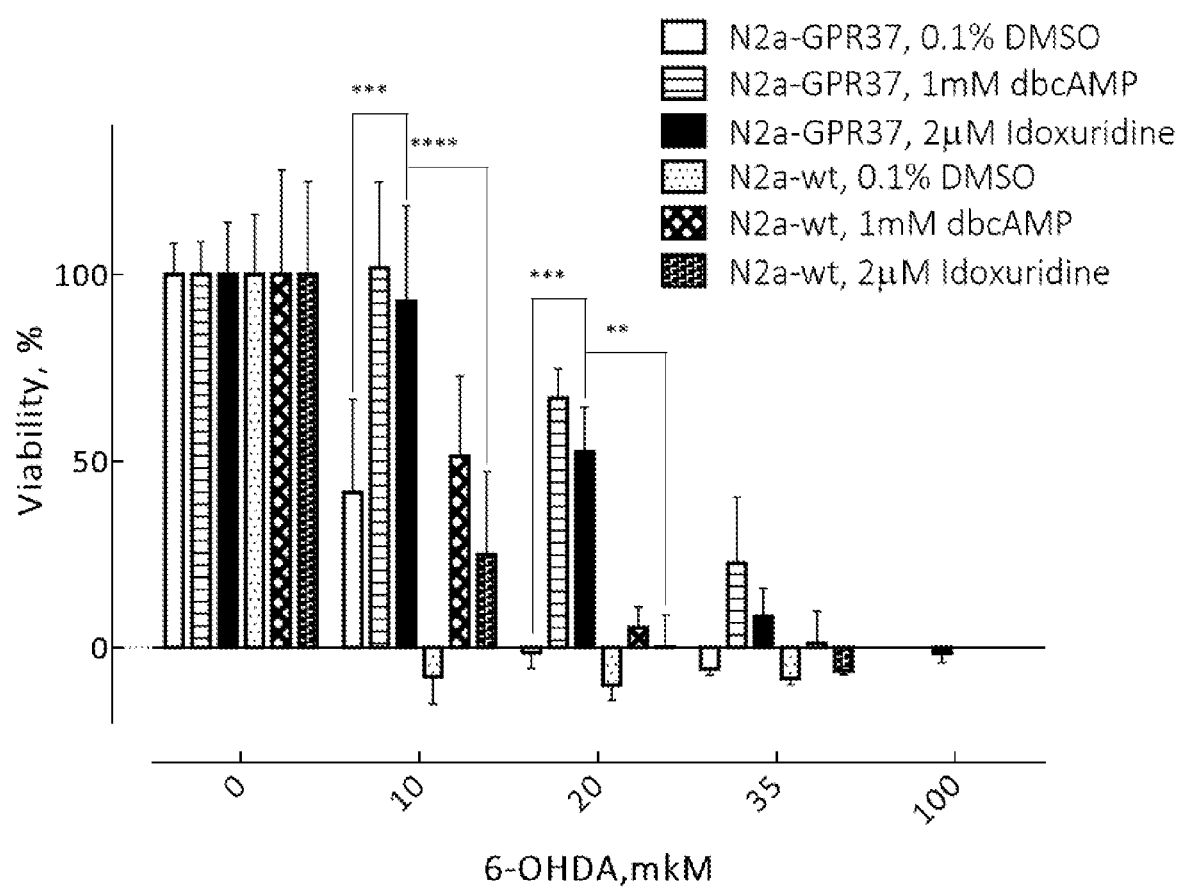
FIG. 6. GPR37-associated cytoprotection of Idoxuridine against parkinsonian drug 6-OHDA. N2a-WT and N2a-GPR37-tGFP cells were grown in differentiating medium containing either 2 µM idoxuridine, 0.1% DMSO (negative control) or 1 mM dbcAMP (positive control). 72 h later cells were treated with either 6-OHDA (10, 20, 35 100 µM) or vehicle control and incubated for 24 h. Cell viability was quantified by MTT assay. Data are pooled from three independent experiments with 6 technical replicates for each condition and are expressed as means+/−SD. To assess the cryoprotective effect of idoxuridine against 6-OHDA-toxicity data were analyzed using a 2-way ANOVA followed by a Bonferroni correction test. Each cell line was statistically analyzed separately, with pretreatment and 6-OHDA treatment as variables; or GPR37 expression and 6-OHDA-treatment as variables. For simplicity, only idoxuridine related significance is indicated; significances between positive and negative controls are not shown; **p<0.0001, *p<0.001, **p<0.01.

Results:
The GPR37-specific cytoprotective effect of idoxuridine was evaluated by comparing N2a-GPR37-tGFP cells with N2a-WT cells. The results show that pretreatment with idoxuridine is, in fact, protective for both cell lines but with significantly higher effect on cells stably expressing GPR37-tGFP (FIG. 6). The observed positive effect on N2a-WT cells might be the consequence of certain level of GPR37, since GPR37 is endogenously expressed by this cell line.

(b) NMDA
Primary cortical neurons: Primary cortical neurons were prepared from E18 rat embryos. Cortices were isolated, cleared from meninges and dissociated after incubation in HBSS ($Ca^{2+}$ and $Mg^{2+}$-free) with 0.25% trypsin for 20 min at 37° C. Following washing with $Ca^{2+}/Mg^{2+}$-free HBSS, cells were disaggregated in the presence of 0.1% of DNAse and resuspended in DMEM supplemented with 10% fetal bovine serum (FBS), antibiotics (100 U/ml penicillin, 100 µg/ml streptomycin) and 0.8 mM glutamine. Subsequently neurons were plated on poly-D-lysine-coated glass coverslips (round 12 mm, A. Hartenstein GmbH) in density of 50.000 cells/cov. 24 hours after the plating, DMEM was exchanged with Neurobasal medium supplemented with B27, antibiotics and 0.8 mM glutamine. Cells were kept in a humidified incubator with 5% $CO_2$ until used.

Cell Toxicity:
Mature primary neurons were pretreated with Idoxuridine (25 µM) or DMSO (ctrl cells) for 72 h or 48 h and subsequently exposed to NMDA (200 µM) for 30 min. Cell viability was assessed by propidium iodide (PI) staining. Both control and treated cells were incubated for 30 min with 6 µM PI which stains nuclei of dead cells. After extensive washing with Tyrode's buffer, samples were fixed and stained with DAPI to visualize all cell nuclei. PI positive cells were counted at several regions on coverslips and expressed as percentage of total cells visualized with DAPI stain. Cells fixed with PFA before PI staining were used as positive control.

Figure 7:
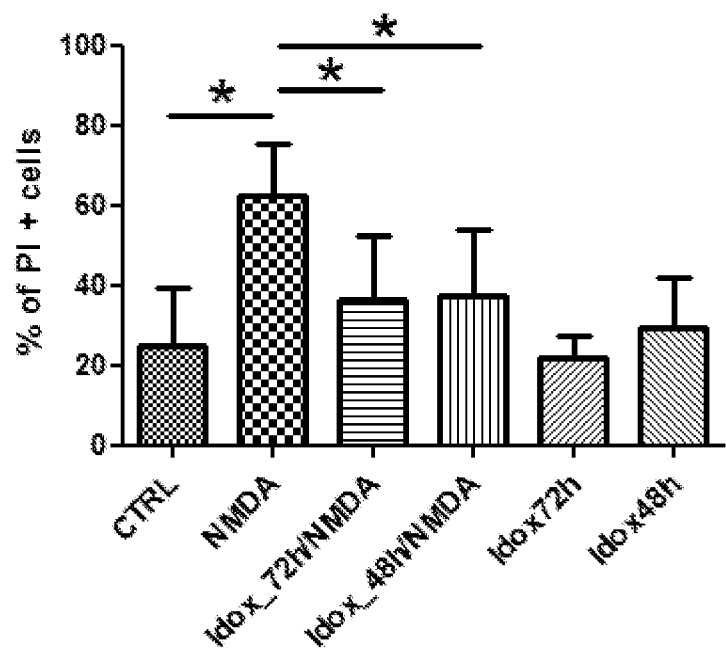
FIG. 7: Cytoprotection of Idoxuridine against excitotoxicity of NMDA. Mature primary neurons were pretreated with Idoxuridine (25 µM) or DMSO (ctrl cells) for 72 h or 48 h and subsequently exposed to NMDA (200 µM) for 30 min. Cell viability was assessed by propidium iodide (PI) staining. Both control and treated cells were incubated for 30 min with 6 µM PI which stains nuclei of dead cells. After extensive washing with Tyrode's buffer, samples were fixed and stained with DAPI to visualize all cell nuclei. PI positive cells were counted at several regions on coverslips and expressed as percentage of total cells visualized with DAPI stain. Excitotoxicity was induced with NMDA and was significantly counteracted by Idoxuridine. Data are expressed as means+/−SD and analyzed by one-way ANOVA with Dunnett's posthoc test. *p<0.001

As shown in FIG. 7, excitotoxicity induced by NMDA was significantly counteracted by pretreatment with Idoxuridine.

Figure 8:
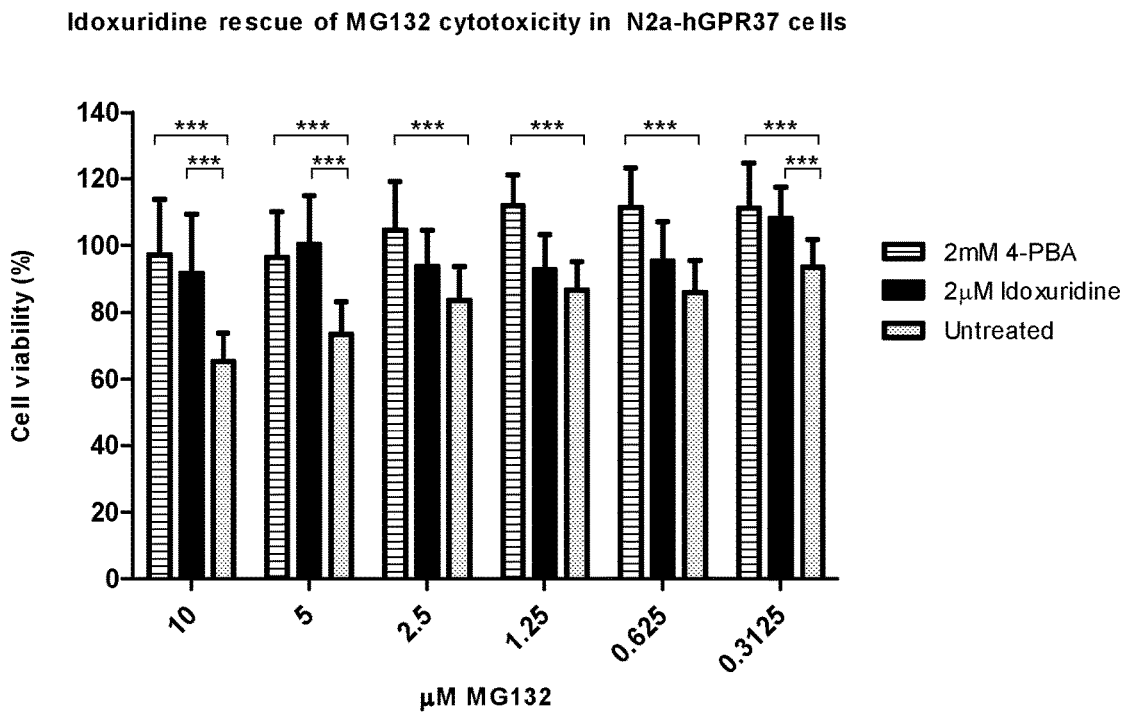
FIG. 8: Cytoprotection of Idoxuridine against MG132. MG132-induced proteasomal inhibition reduced cell viability. This effect was potently counteracted in GPR37-tGFP overexpressing cells (A) and also showed some neuroprotection in wildtype cells. Data represented as mean+SD. Analysis performed via one-way ANOVA with Neuman-Keuls post-test for both Figures. *** indicates p<0.001. 2 mM 4-PBA used as a positive unspecific control.
Figure 8:
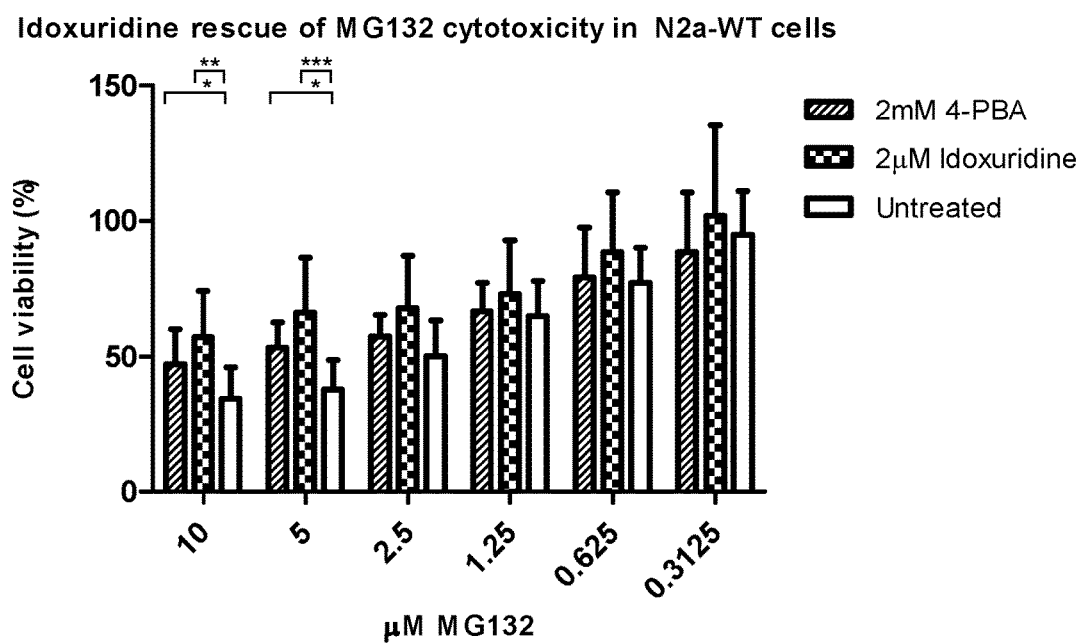

(c) MG132
MG132 is a potent 26S proteasome inhibitor which increases protein accumulation, ROS leakage, induces cell cycle arrest and apoptosis. As shown in FIG. 8, MG132-induced proteasomal inhibition reduced cell viability. This effect was potently counteracted in GPR37-tGFP overexpressing cells (A) and also showed some neuroprotection in wildtype cells.

Figure 9:
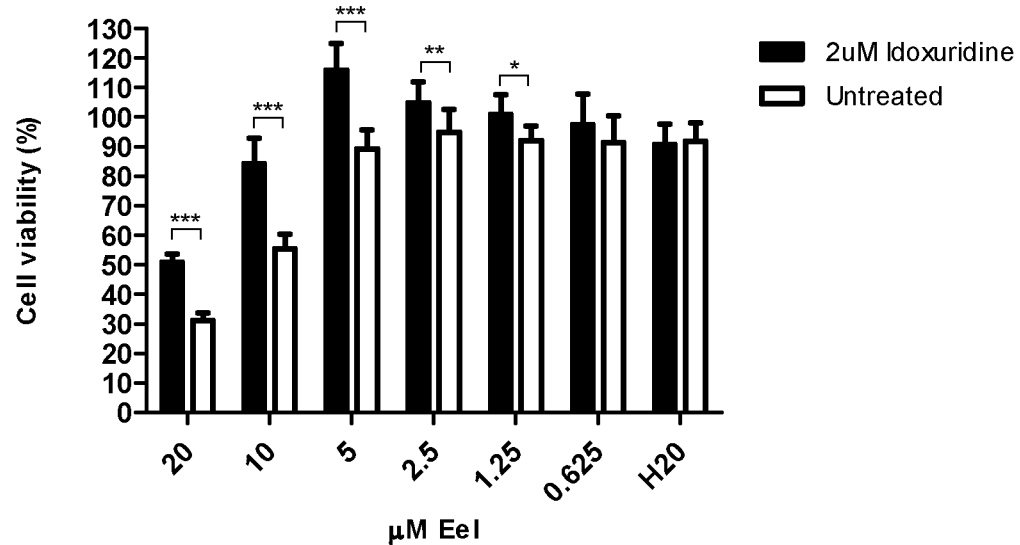
FIG. 9: Cytoprotection of Idoxuridine against Eel. Eeyarestatin (Eel) is a potent inhibitor of endoplasmic reticulum associated protein degradation (ERAD) pathway, specifically targeting p97. Eel-mediated reduction of cell viability is counteracted by idoxuridine in both GPR37-tGFP overexpressing cells (A) and WT (B) cells. Data represented as mean+SD. Analysis performed via one-way ANOVA with Neuman-Keuls post-test for both Figures. *** indicates p<0.001.
Figure 9:
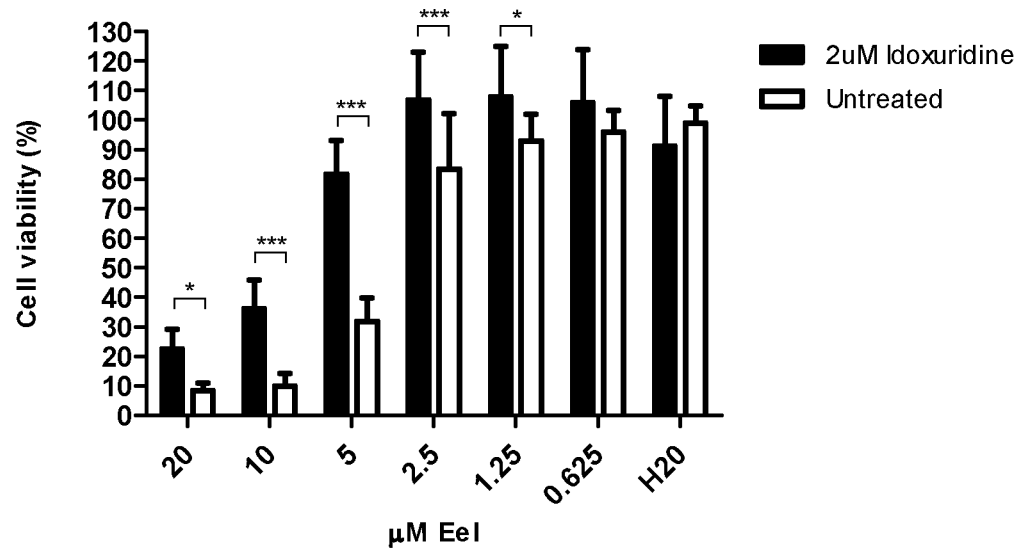

(d) EeI
Eeyarestatin (EeI) is a potent inhibitor of endoplasmic reticulum associated protein degradation (ERAD) pathway, specifically targeting p97. As shown in FIG. 9, EeI-mediated reduction of cell viability is counteracted by idoxuridine in both GPR37-tGFP overexpressing cells (A) and WT (B) cells.

Figure 10:
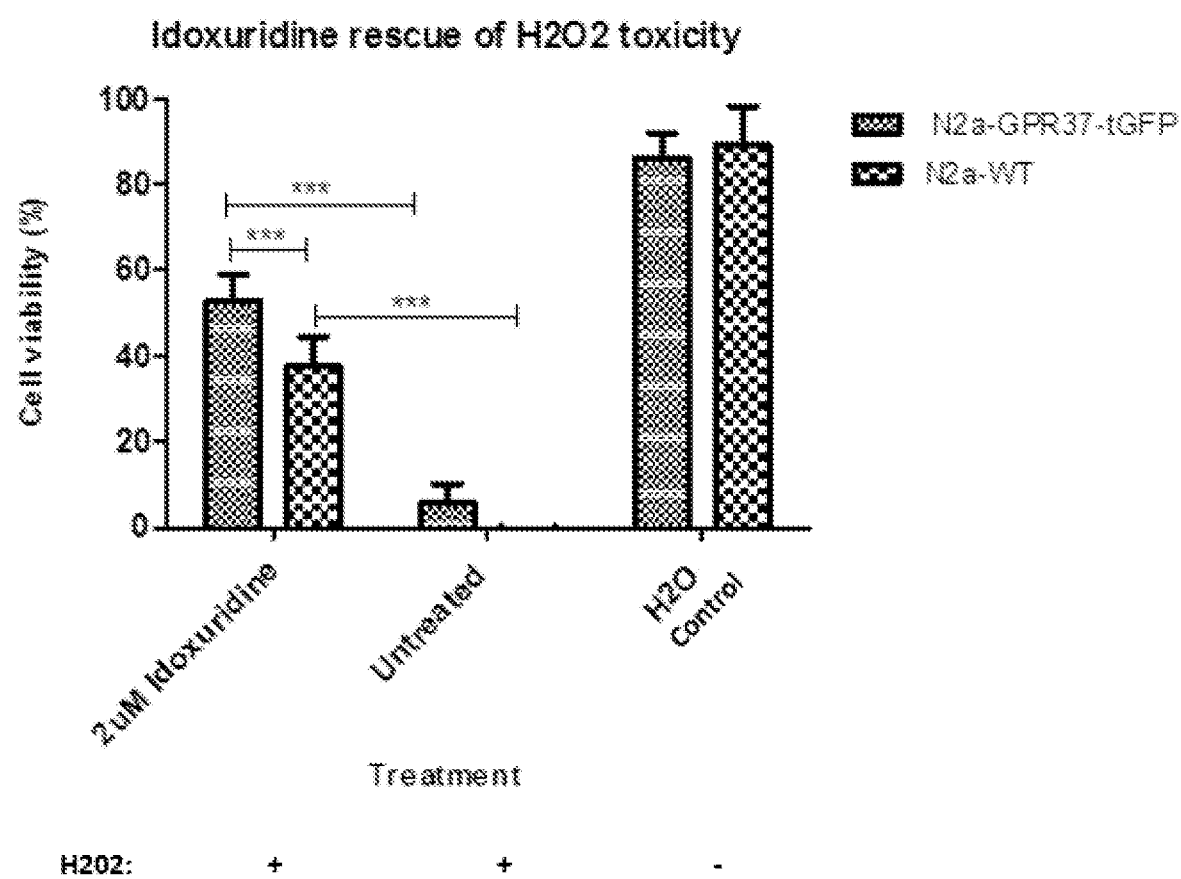
FIG. 10: Cytoprotection of Idoxuridine against 11202. $H_2O_2$ reduces cell viability by increasing oxidative stress. This effect was counteracted by idoxuridine in GPR37-tGFP overexpressing cells (A) and WT (B) cells. The effect was significantly stronger in GPR37-tGFP overexpressing cells. In-well $H_2O_2$ concentration used was 0.00025%. Untreated N2a-WT cells showed unmeasurably low levels of viability.

(e) $H_2O_2$
As shown in FIG. 10, $H_2O_2$ reduces cell viability by increasing oxidative stress. This effect was counteracted by idoxuridine in GPR37-tGFP overexpressing cells (A) and WT (B) cells. The effect was significantly stronger in GPR37-tGFP overexpressing cells.

Example 4: Translocation Assay with Idoxuridine Analogs 24 idoxuridine analogs (FIG. 11) were provided by the Chemical Biology Consortium Sweden (CBCS) and were tested at three concentrations (2, 10 and 20 µM) in the GPR37-translocation assay disclosed above. One compound, no. 17 (2'-deoxy-5-(3-aminophenyl)-uridine), showed up as a strong hit and two others, compound 4 (2'-deoxy-5-ethynyluridine) and compound 2 (2'-deoxy-5-hydroxyuridine), showed a slight positive effect.

Figure 11:
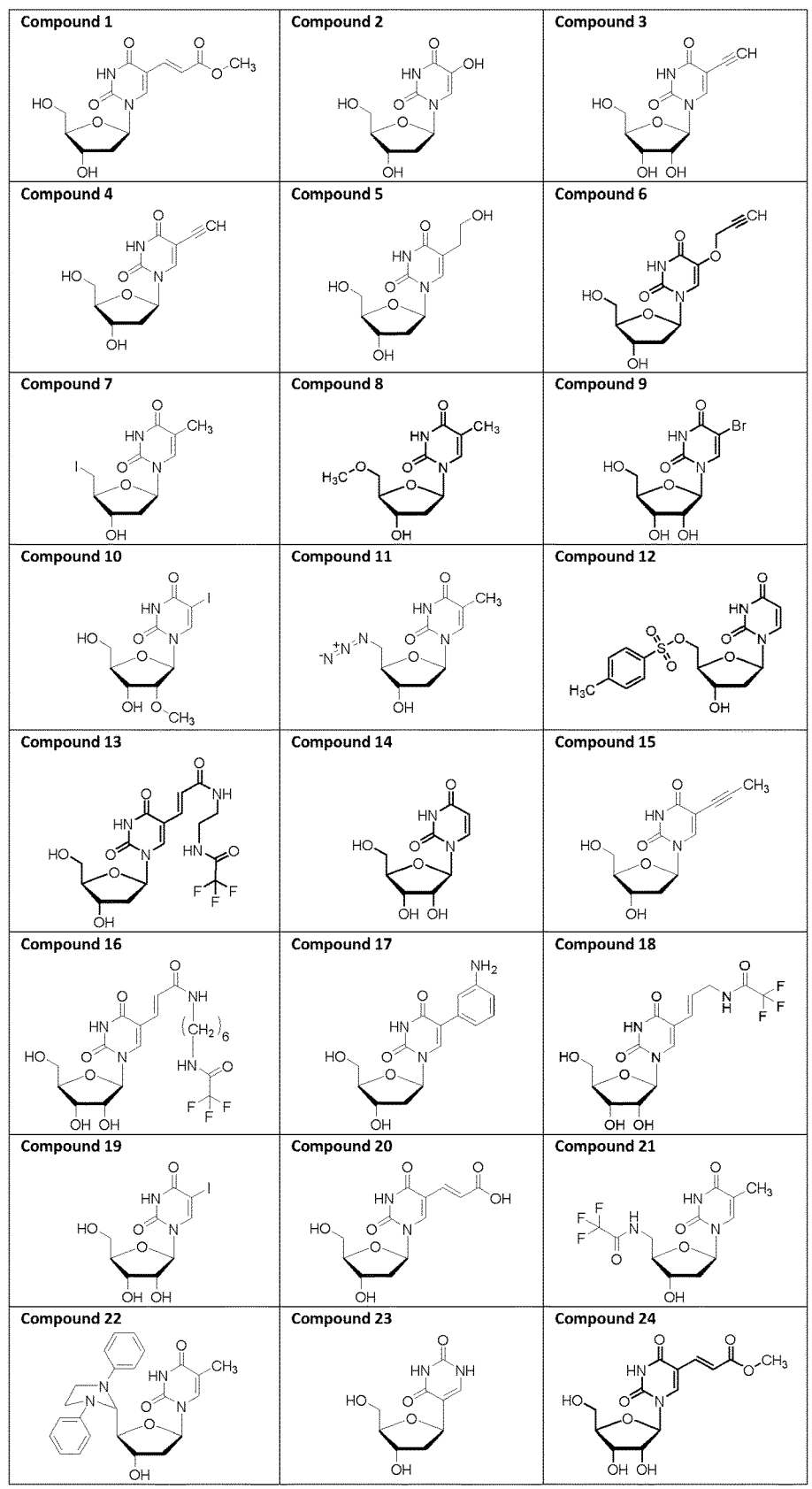
FIG. 11. Structures of Idoxuridine analogs tested in GPR37-tGFP translocation assay. See Example 4 for details.

The IUPAC names of the compounds shown in FIG. 11 are as follows:
1. methyl (E)-3-(1-((2R,4S,5R)-4-hydroxy-5-(hydroxymethyl) tetra-hydrofuran-2-yl)-2,4-dioxo-1,2,3,4-tetrahydropyrimidin-5-yl)acrylate.
2. 5-hydroxy-1-((2R,4S,5R)-4-hydroxy-5-(hydroxymethyl) tetrahydrofuran-2-yl)pyrimidine-2,4(1H,3H)-dione.
3. 1-((2R,3R,4S,5R)-3,4-dihydroxy-5-(hydroxymethyl)-tetrahydrofuran-2-yl)-5-ethynylpyrimidine-2,4(1H,3H)-dione.
4. 5-ethynyl-1-((2R,4S,5R)-4-hydroxy-5-(hydroxymethyl)-tetrahydrofuran-2-yl)pyrimidine-2,4(1H,3H)-dione.
5. 1-((2R,4S,5R)-4-hydroxy-5-(hydroxymethyl)tetrahydrofuran-2-yl)-5-(2-hydroxyethyl)pyrimidine-2,4(1H,3H)-dione.
6. 1-((2R,4S,5R)-4-hydroxy-5-(hydroxymethyl)tetrahydrofuran-2-yl)-5-(prop-2-yn-1-yloxy)pyrimidine-2,4(1H,3H)-dione.
7. 1-((2R,4S,5S)-4-hydroxy-5-(iodomethyl)tetrahydrofuran-2-yl)-5-methylpyrimidine-2,4(1H,3H)-dione.
8. 1-((2R,4S,5R)-4-hydroxy-5-(methoxymethyl)tetrahydrofuran-2-yl)-5-methylpyrimidine-2,4(1H,3H)-dione.
9. 5-bromo-1-((2R,3R,4S,5R)-3,4-dihydroxy-5-(hydroxymethyl)tetrahydrofuran-2-yl)pyrimidine-2,4(1H,3H)-dione.

10. 1-((2R,3R,4R,5R)-4-hydroxy-5-(hydroxymethyl)-3-methoxy-tetrahydrofuran-2-yl)-5-iodopyrimidine-2,4 (1H,3H)-dione.
11. 3-(((2S,3R,5S)-3-hydroxy-5-(5-methyl-2,4-dioxo-3,4-dihydropyrimidin-1(2H)-yl)tetrahydrofuran-2-yl) methyl)-214-triaza-1,2-dien-1-ide.
12. ((2R,3S,5R)-5-(2,4-dioxo-3,4-dihydropyrimidin-1 (2H)-yl)-3-hydroxytetrahydrofuran-2-yl)methyl 4-methyl-benzenesulfonate.
13. (E)-3-(1-((2R,4S,5R)-4-hydroxy-5-(hydroxymethyl)-tetrahydrofuran-2-yl)-2,4-dioxo-1,2,3,4-tetrahydro-pyrimidin-5-yl)-N-(2-(2,2,2-trifluoroacetamido)-ethyl)acrylamide.
14. 1-((2R,3R,4S,5R)-3,4-dihydroxy-5-(hydroxymethyl)-tetrahydrofuran-2-yl)pyrimidine-2,4(1H,3H)-dione.
15. 1-((2R,4S,5R)-4-hydroxy-5-(hydroxymethyl)tetrahydrofuran-2-yl)-5-(prop-1-yn-1-yl)pyrimidine-2,4(1H,3H)-dione.
16. (E)-3-(1-((2R,3R,4S,5R)-3,4-dihydroxy-5-(hydroxymethyl)tetrahydrofuran-2-yl)-2,4-dioxo-1,2,3,4-tetrahydropyrimidin-5-yl)-N-(6-(2,2,2-trifluoroacetamido)hexyl) acrylamide.
17. 5-(3-aminophenyl)-1-((2R,4S,5R)-4-hydroxy-5-(hydroxy-methyl)tetrahydrofuran-2-yl)pyrimidine-2,4(1H, 3H)-dione.
18. N-((E)-3-(1-((2R,3R,4S,5R)-3,4-dihydroxy-5-(hydroxymethyl)tetrahydrofuran-2-yl)-2,4-dioxo-1,2,3,4-tetrahydropyrimidin-5-yl)allyl)-2,2,2-trifluoroacetamide.
19. 1-((2R,3R,4S,5R)-3,4-dihydroxy-5-(hydroxymethyl)-tetrahydrofuran-2-yl)-5-iodopyrimidine-2,4(1H,3H)-dione.
20. (E)-3-(1-((2R,4S,5R)-4-hydroxy-5-(hydroxymethyl)-tetrahydrofuran-2-yl)-2,4-dioxo-1,2,3,4-tetrahydropyrimidin-5-yl)acrylic acid.
21. 2,2,2-trifluoro-N-(((2R,3S,5R)-3-hydroxy-5-(5-methyl-2,4-dioxo-3,4-dihydropyrimidin-1(2H)-yl)tetrahydrofuran-2-yl)methyl)acetamide.
22. 1-((2R,4S,5R)-5-(1,3-diphenylimidazolidin-2-yl)-4-hydroxytetrahydrofuran-2-yl)-5-methylpyrimidine-2,4(1H, 3H)-dione.
23. 5-((2R,4S,5R)-4-hydroxy-5-(hydroxymethyl)tetrahydrofuran-2-yl)pyrimidine-2,4(1H,3H)-dione.
24. methyl (E)-3-(1-((2R,3R,4S,5R)-3,4-dihydroxy-5-(hydroxymethyl)tetrahydrofuran-2-yl)-2,4-dioxo-1,2,3,4-tetrahydropyrimidin-5-yl)acrylate.

Example 5: Synthesis of Ropidoxuridine

Nucleosides are classically synthesized using silyl-Hilbert-Johnson coupling of a silylated heterocyclic purine or pyrimidine base, and a ribose or deoxyribose derivative. The resulting nucleoside, or deoxynucleoside, is usually obtained as a mixture of α- and β-anomers in various ratios depending on reaction conditions and structural features of the nucleophilic, heterocyclic base and the electrophilic sugar moiety.

It is generally recognized that syntheses of 2'-deoxynucleosides are among the most difficult in nucleoside chemistry and often frequently low yielding. (Ref 24) The main synthetic difficulties posed by 2'-deoxynucleosides, of which ropidoxuridine is a member, are: (a) low stability of electrophilic partners, i.e. 2'-deoxysugars, such as Hoffer's sugar (3a); (b) low total yields of the anomeric mixtures of β-anomer and α-anomer; and (c) low ratios of the desired β-anomer to the unwanted α-anomer.

Figure 13:
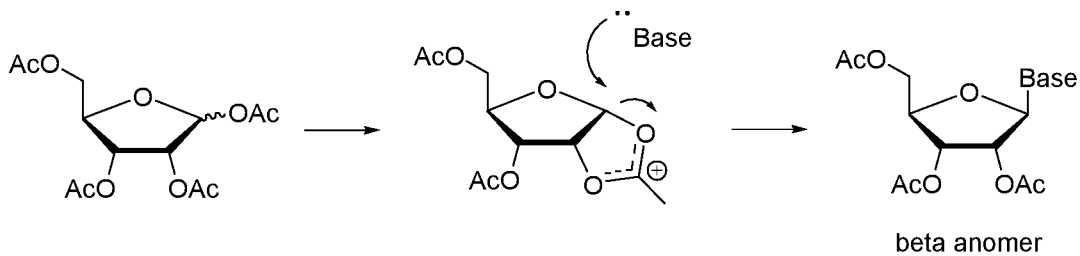
FIG. 13. Mechanism for anchimeric assistance during glycosylation reaction of nucleoside and glycosylation reaction of 2'-deoxynucleoside. See Example 5 for details.
Figure 13:
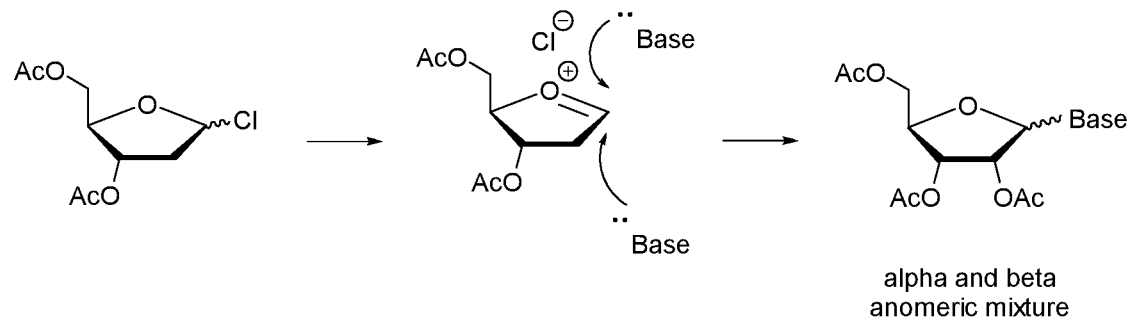

Moreover, the expensive 1-α-chlorosugars such as (3a) are prone to decomposition and epimerization, especially in polar solvents and/or in the presence of Lewis acids, leading to the thermodynamically more stable 1-β-chlorosugars. Furthermore, when anchimeric groups are present in the nucleoside, participation of the neighboring 2'-carboxy group directs the glycosidation exclusively from the top face leading to the desired β-anomer stereoselectively (FIG. 13). However, 2'-deoxynucleosides, such as ropidoxuridine, lack the anchimeric 2'-group, resulting in mixtures of anomers, frequently with the undesired α-anomer as major product.

Figure 12:
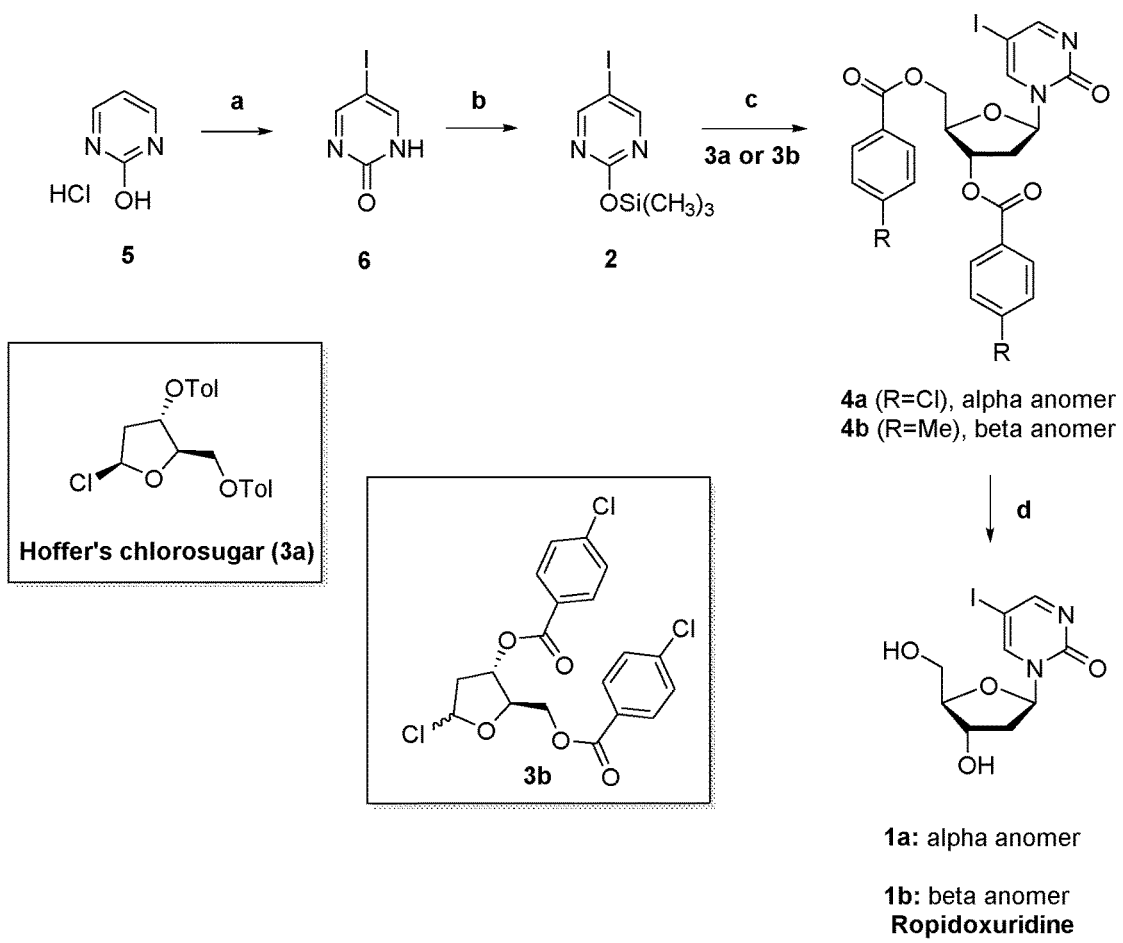
FIG. 12. Synthesis of ropidoxuridine. See Example 5 for details.

Synthesis of the 2'-deoxynucleoside ropidoxuridine (also known as 1-((2R,4S,5R)-4-hydroxy-5-(hydroxymethyl)tetrahydrofuran-2-yl)-5-iodopyrimidin-2(1H)-one, compound 1b) have previously been published by two research groups (Ref. 25 and 26). In both instances, tin tetrachloride-catalyzed silyl-Hilbert-Johnson coupling of 5-iodo-2-((trimethylsilyl)oxy)pyrimidine (2) with chlorosugar (3b) in 1,2-dichloro-ethane was used as key step (step c, FIG. 12). However, these procedures could not be employed to obtain the required β-anomer 5-(5-iodo-2-oxopyrimidin-1(2H)-yl)-2-(((4-methylbenzoyl)oxy)-methyl)tetrahydrofuran-3-yl 4-methylbenzoate (4) in sufficient quantities. There are several drawbacks in these previously reported procedures. First, the inventors' attempts to reproduce the tin(IV) chloride catalyzed coupling resulted in emulsions during workup which were very difficult to extract with dichloromethane. Indeed, the use of tin (IV) chloride as catalyst is known to give rise to problematic emulsions and colloids during aqueous work-up. (Ref 27) Second, tin (IV) chloride is not suitable for the manufacture of Active Pharmaceutical Ingredients (APIs) for human use due to its toxicity and frequent difficulties in removal of its residues. Third, both methods employ 1,2-dichloroethane as solvent which is no longer used due to its ICH Class 1 solvent classification (Ref 28).

Thus, there is an unmet need in the field for the provision of a method for preparation of ropidoxuridine that provides an API that is suitable for use in humans, minimizes the exposure to toxic heavy metals and is more environmentally friendly due to the use of less toxic solvents.

The present invention provides for the first time a practical method to ropidoxuridine without the use of tin catalysts thereby avoiding the formation of intractable emulsions during workup of the key coupling reaction. The method provides a product free from heavy metal residues and is therefore suitable for use in humans. Moreover, ICH Class 1 solvent 1,2-dichloroethane has been substituted with environmentally less deleterious chloroform.

Ropidoxuridine was synthesized according to the following process:

According to reaction scheme (FIG. 12), iodination of 2-hydroxy-pyrimidine (5) hydrochloride using silver(I) sulfate and iodine gave 5-iodopyrimidin-2(1H)-one (6) (Step a) in 94% yield. The valuable silver(I)iodide was recovered by vacuum filtration and stored in the dark. 5-iodo-pyrimidin-2(1H)-one (6) was then silylated using 10 equivalents hexamethyl-disilazane and 1 equivalent trimethylsilyl chloride to provide 5-iodo-2-((trimethyl-silyl)oxy)pyrimidine (2) in quantitative yield (Step b). This moisture sensitive silane was to be used directly in the next coupling step (Step c).

Hoffer's chloro-sugar (Ref 29) (3a) was prepared via a three-step sequence according to Kotera (Ref. 30) and coworkers, who improved upon Hoffer's original protocol. CuI catalysis has previously been applied to couple bis (trimethilsilyl)oxy pyrimidines with halosugars (Ref. 31). However, we have now shown that CuI catalysis can be extended to considerably less nucleophilic mono(trimethilsilyl)oxy pyrimidines, such as 5-iodo-2-((trimethyl-silyl) oxy)pyrimidine (2), albeit in lower yield. Thus, Hoffer's sugar (3a) was coupled with 5-iodo-2-((trimethyl-silyl)oxy)-pyrimidine (2) affording key intermediate (4b) in 31% yield. In order to increase the anomeric ratio, as well as the yield of the β-anomer (1b), it was essential to use excess (≥2 eq.) 5-iodo-2-((trimethylsilyl)oxy)pyrimidine (2) during the glycosylation reaction. When using equimolar amount, or a slight excess, of 5-iodo-2-((trimethylsilyl)oxy)-pyrimidine (2), only trace amounts of β-anomer 1b could be isolated. Moreover, we have demonstrated that the key coupling step could be performed without metal catalysis to give β-anomer 4b in 19% yield. Finally, cleavage of the toluoyl protecting groups of 4b, using a saturated solution of ammonia in methanol afforded the β-anomer 1b, ropidoxuridine, in 42% yield.

The α-anomer (4a) was prepared in good yield (59%) from 5-iodo-2-((trimethyl-silyl)oxy)-pyrimidine (2) and chlorosugar (3b) using a tin(IV) chloride promoted coupling in dichloromethane. Deprotection of 4a with methanolic ammonia gave the α-anomer 1a in 62% yield.

Preparation of 5-iodopyrimidin-2(1H)-one (6)

To a solution of pyrimidin-2-ol hydrochloride (5) (12.306 g, 93 mmol) in methanol (357 ml) was added iodine (27.2 g, 107 mmol). The dark purple mixture was stirred at room temperature until all iodine had dissolved. Pulverized silver (I) sulfate (33.4 g, 107 mmol) was added, in one portion, and the mixture was allowed to stir for 16 h in the dark. The yellow AgI precipitate was filtered and the filter cake washed with methanol. The filtrate was treated dropwise with a 50% aq. KOH solution until pH 10 forming a heavy white precipitate. The resulting alkaline mixture was neutralized (pH 7) with acetic acid and rotoevaporated to dryness in vacuo. The solid residue was suspended in boiling water (~500 mL) and allowed to boil for 30 minutes. Additional water was added portion wise and the heating was continued until a yellow solution was obtained. The solution was allowed to cool to room temperature and placed in fridge for three days. The resulting suspension was filtered with suction, washed with cold water and dried to give compound 6, 5-iodopyrimidin-2(1H)-one (19.34 g, 87 mmol, 94% yield) as a yellow solid. $^1$H NMR (500 MHz, DMSO-$d_6$) δ 8.43 (s, 2H), 12.21 (s, 1H); LRMS (ESI) [M−H]$^−$ calculated for $C_{12}$ $^{13}C_4H_3IN_2O$ 221.9, found 220.9.

Preparation of Silylated 5-iodopyrimidin-2(1H)-one (2)

To a suspension of 5-iodopyrimidin-2(1H)-one (6) (10 g, 45.0 mmol) in HMDS (94 ml, 450 mmol) was added TMS-Cl (5.76 ml, 45.0 mmol). The resulting suspension was allowed to reflux for 2 h (external temperature +135° C.), during which time all starting material had gone into the solution and ammonium chloride was the only remaining solid. The reaction was allowed to cool and HMDS was removed under vacuum, breaking the vacuum with nitrogen. The remaining brown oil was co-evaporated with dry toluene twice in order to ensure the complete removal of HMDS. Under nitrogen atmosphere, the oily product was dissolved in toluene, taken up in a syringe and filtered using a 0.45 μm syringe filter to remove solids. The toluene was evaporated in vacuo to provide compound 2, 5-iodo-2-((trimethylsilyl)oxy)pyrimidine (13.17 g, 44.8 mmol, 99% yield) as a brown oil which was used directly in next step as it decomposes on contact with air.

Tin(IV)Chloride-Catalyzed Coupling of Silylated 5-iodopyrimidin-2(1H)-one; Synthesis of Protected α-Anomer 4a To a cooled (−35° C. internal temperature) solution of 5-iodo-2-((trimethylsilyl)oxy)-pyrimidine (2) (0.397 g, 1.351 mmol) in anhydrous dichloromethane (10 ml) under nitrogen was added, in one portion, 5-chloro-2-(((4-chlorobenzoyl)oxy)methyl)-tetrahydrofuran-3-yl 4-chlorobenzoate (3) (0.580 g, 1.351 mmol). The resulting solution was kept at −30° C. under stirring and at this temperature treated with a solution of tin(IV) chloride (0.600 ml, 0.600 mmol) in anhydrous dichloromethane (5 mL). After 1 h and 30 minutes, the mixture was poured on cold sat. NaHCO$_3$ solution (50 mL) and dichloromethane (60 mL) and stirred vigorously for 30 min to destroy all tin(IV) chloride. The mixture was filtered over Celite and the filter cake was washed 3 times with fresh dichloromethane. The filtrate formed an emulsion. The phases were separated, the organic phase was washed with water (200 mL) twice and dried over anhydrous sodium sulfate. The solvents were removed under reduced pressure to give 0.644 g solid which was sonicated in 10 mL isopropyl alcohol and filtered. The α-anomer, 4a, ((2R,3S,5S)-3-((4-chlorobenzoyl)oxy)-5-(5-iodo-2-oxopyrimidin-1(2H)-yl)tetrahydrofuran-2-yl)methyl 4-chlorobenzoate was obtained as a white solid (0.488 g, 0.793 mmol, 58.7% yield). $^1$H NMR (500 MHz, DMSO-$d_6$) δ 8.63 (s, 1H), 8.18 (s, 1H), 7.97 (d, 2H), 7.69 (d, 2H), 7.46-7.41 (m, 4H), 6.26 (d, 1H), 5.64 (d, 1H), 5.01 (t, 1H), 4.54 (dd, 2H), 3.01-2.96 (m, 1H), 2.67 (d, 1H); [M+H]$^+$ calculated for $C_9H11IN2O4$ 338.0, found 339.0.

Deprotection of Protected α-Anomer; Synthesis of α-Anomer 1a

To a vial containing ((2R,3S,5S)-3-((4-chlorobenzoyl)oxy)-5-(5-iodo-2-oxopyrimidin-1(2H)-yl)tetrahydrofuran-2-yl)methyl 4-chlorobenzoate (4a) (0.206 g, 0.335 mmol) cooled on ice, was added a cold, saturated solution of ammonia (12 ml, 96 mmol) in methanol. As soon as a clear solution was obtained the sealed vial was placed in refrigerator for 24 h. After this time the methanolic ammonia was evaporated in vacuo to give a solid. The crude product was triturated in boiling acetone, allowed to cool to room temperature and placed in freezer (−25° C.) for 12 h. The suspension was filtered with suction, washed with cold acetone and dried to give α-anomer 1a, 1-((2S,4S,5R)-4-hydroxy-5-(hydroxymethyl)tetrahydrofuran-2-yl)-5-iodopyrimidin-2(1H)-one, (0.070 g, 0.208 mmol, 62% yield). $^1$H NMR (500 MHz, DMSO-$d_6$) δ 8.62 (s, 1H), 8.32 (s, 1H), 5.95 (d, 1H), 5.17 (s, 1H), 4.91 (t, 1H), 4.36 (t, 1H), 4.22 (s, 1H), 3.46-3.41 (m, 2H), 2.59-2.54 (m, 1H), 2.00-1.98 (m, 1H); LRMS (ESI) [M+H]$^+$ calculated for $C_{23}H_{17}Cl_2IN_2O_6$ 614.0 found 615.0.

CuI-Catalyzed Coupling of Silylated 5-iodopyrimidin-2(1H)-one; Synthesis of Protected β-Anomer 4b Under a nitrogen atmosphere, a stirred solution of 5-iodo-2-((trimethylsilyl)oxy)-pyrimidine (2) (3 g, 10.20 mmol) in dry, and ethanol free, chloroform (130 ml) was treated with freshly prepared (2R,3S,5R)-5-chloro-2-(((4-methylbenzoyl)oxy)methyl) tetrahydrofuran-3-yl 4-methylbenzoate (3, R=Me) (1.983 g, 5.10 mmol). As soon the chlorosugar (3a) had dissolved, copper(I) iodide (0.971 g, 5.10 mmol) was added in one portion. The mixture was stirred at room temperature for 24 h and filtered with suction to remove CuI. The filtrate was treated with methanol (1 mL) at which point remaining equivalent 5-iodopyrimidin-2(1H)-one (6) precipitated out. The resulting suspension was filtered with suction and the filtrate reduced in vacuo to give a yellow foam. The crude product was added to a silica gel column and was eluted with 10% EtOAc in DCM to afford the faster moving β-anomer 4b, (2R,3S,5R)-5-(5-iodo-2-oxopyrimidin-1(2H)-yl)-2-(((4-methylbenzoyl)oxy)methyl)tetrahydrofuran-3-yl 4-methylbenzoate, (0.908 g, 1.581 mmol, 31% yield) as off-white crystals. $^1$H NMR (500 MHz, CDCl$_3$) δ 8.58 (s, 1H), 8.29 (s, 1H), 7.96 (d, 2H), 7.80 (d, 2H), 7.29 (d, 2H), 7.26 (d, 2H), 6.28 (t, 1H), 5.62 (d, 1H), 4.85-4.81 (m, 1H), 4.71-4.61 (m, 2H), 3.18 (dd, 1H), 2.45 (s, 3H), 2.43 (s, 3H), 2.27-2.21 (m, 1H); LRMS (ESI) [M+H]$^+$ calculated for $C_{25}H_{23}IN_2O_6$ 574.1, found 575.1.

Metal-Free Coupling of Silylated 5-iodopyrimidin-2(1H)-one; Synthesis of Protected β-Anomer 4b Under a nitrogen atmosphere, a stirred solution of 5-iodo-2-((trimethylsilyl)oxy)-pyrimidine (2) (2 g, 6.8 mmol) in dry, and ethanol free, chloroform (45 ml) was treated with freshly prepared (2R,3S,5R)-5-chloro-2-(((4-methylbenzoyl)oxy)methyl) tetrahydrofuran-3-yl 4-methylbenzoate (3, R=Me) (0.661 g, 1.7 mmol). The clear solution was stirred at room temperature for 24 h and quenched with methanol (1 mL) at which point remaining equivalent 5-iodopyrimidin-2(1H)-one (6) precipitated out. The resulting suspension was filtered with suction and the filtrate reduced in vacuo to give a yellow residue. The crude product was added to a silica gel column and was eluted with 10% EtOAc in DCM to afford the faster moving β-anomer 4b, (2R,3S,5R)-5-(5-iodo-2-oxopyrimidin-1(2H)-yl)-2-(((4-methylbenzoyl)oxy)-methyl)tetrahydrofuran-3-yl 4-methylbenzoate, (0.185 g, 0.323 mmol, 19% yield) as off-white crystals. NMR data and LRMS data in accordance with previous experiment.

Deprotection of Protected β-Anomer; Synthesis of β-Anomer 1b, Ropidoxuridine

To a vial containing (2R,3S,5R)-5-(5-iodo-2-oxopyrimidin-1(2H)-yl)-2-(((4-methylbenzoyl)oxy)methyl)tetrahydrofuran-3-yl 4-methylbenzoate (0.692 g, 1.205 mmol) (4b) cooled on ice, was added a cold, saturated solution of ammonia (45.2 ml, 361 mmol) in methanol. As soon as a clear solution was obtained the sealed vial was placed in refrigerator for 24 h. After this time the methanolic ammonia was evaporated in vacuo to give a yellow wax. The crude product was added to a silica gel column and was eluted with 5% MeOH in DCM to afford a solid which still contained impurities. The yellow solid was suspended in boiling EtOAc (5 mL), allowed to cool to room temperature and placed in freezer (−25° C.) for 12 h. The suspension was filtered with suction, washed with cold EtOAc and dried to give β-anomer 1b (ropidoxuridine) 1-((2R,4S,5R)-4-hydroxy-5-(hydroxymethyl)tetrahydrofuran-2-yl)-5-iodopyrimidin-2(1H)-one (171 mg, 0.444 mmol, 41.7% yield). $^1$H NMR (500 MHz, mixture of DMSO-d$_6$ and D$_2$O) δ 8.72 (d, J=3 Hz, 1H), 8.65 (d, J=3 Hz, 1H), 6.08 (t, J=5 Hz, J=11.5 Hz, 1H), 5.3 (d, J=4.5 Hz, 1H, OH, D$_2$O exchanged), 5.24 (t, J=4.5 Hz, J=9.5, 1H, OH, D$_2$O exchanged), 4.34 (m, 1H), 4.09 (m, 1H), 3.86 (dd, J=3.5 Hz, 1H), 3.72 (dd, J=4.5 Hz, 1H), 2.59-2.53 (m, 1H), 2.32-2.25 (m, 1H); LRMS (ESI) [M+H]$^+$ calculated for $C_9H_{11}IN_2O_4$ 338.0, found 339.0.

REFERENCES 1. van der Brug, M. P., Singleton, A., Gasser, T., and Lewis, P. A. (2015) Parkinson's disease: From human genetics to clinical trials. Sci Transl Med 7, 205ps220
2. Albanese, A. (2003) Diagnostic criteria for Parkinson's disease. Neurol Sci 24 Suppl 1, S23-26
3. Schulz-Schaeffer, W. J. (2015) Is Cell Death Primary or Secondary in the Pathophysiology of Idiopathic Parkinson's Disease? Biomolecules 5, 1467-1479
4. Murakami, T., Shoji, M., Imai, Y., Inoue, H., Kawarabayashi, T., Matsubara, E., Harigaya, Y., Sasaki, A., Takahashi, R., and Abe, K. (2004) Pael-R is accumulated in Lewy bodies of Parkinson's disease. Ann Neurol 55, 439-442
5. Imai, Y., Soda, M., Inoue, H., Hattori, N., Mizuno, Y., and Takahashi, R. (2001) An unfolded putative transmembrane polypeptide, which can lead to endoplasmic reticulum stress, is a substrate of Parkin. Cell 105, 891-902
6. Zhang, Y., Gao, J., Chung, K. K., Huang, H., Dawson, V. L., and Dawson, T. M. (2000) Parkin functions as an E2-dependent ubiquitin-protein ligase and promotes the degradation of the synaptic vesicle-associated protein, CDCrel-1. Proc Natl Acad Sci USA 97, 13354-13359
7. Wang, H. Q., and Takahashi, R. (2007) Expanding insights on the involvement of endoplasmic reticulum stress in Parkinson's disease. Antioxid Redox Signal 9, 553-561
8. Marazziti, D., Di Pietro, C., Golini, E., Mandillo, S., Matteoni, R., and Tocchini-Valentini, G. P. (2009) Induction of macroautophagy by overexpression of the Parkinson's disease-associated GPR37 receptor. FASEB J 23, 1978-1987
9. Gandia, J., Fernandez-Duenas, V., Morato, X., Caltabiano, G., Gonzalez-Muniz, R., Pardo, L., Stagljar, I., and Ciruela, F. (2013) The Parkinson's disease-associated GPR37 receptor-mediated cytotoxicity is controlled by its intracellular cysteine-rich domain. J Neurochem 125, 362-372
10. Dusonchet, J., Bensadoun, J. C., Schneider, B. L., and Aebischer, P. (2009) Targeted overexpression of the parkin substrate Pael-R in the nigrostriatal system of adult rats to model Parkinson's disease. Neurobiol Dis 35, 32-41
11. Rezgaoui, M., Susens, U., Ignatov, A., Gelderblom, M., Glassmeier, G., Franke, I., Urny, J., Imai, Y., Takahashi, R., and Schaller, H. C. (2006) The neuropeptide head activator is a high-affinity ligand for the orphan G-protein-coupled receptor GPR37. J Cell Sci 119, 542-549
12. Meyer, R. C., Giddens, M. M., Schaefer, S. A., and Hall, R. A. (2013) GPR37 and GPR37L1 are receptors for the neuroprotective and glioprotective factors prosaptide and prosaposin. Proc Natl Acad Sci USA 110, 9529-9534
13. Wang, H., Hu, L., Zang, M., Zhang, B., Duan, Y., Fan, Z., Li, J., Su, L., Yan, M., Zhu, Z., Liu, B., and Yang, Q. (2016) REG4 promotes peritoneal metastasis of gastric cancer through GPR37. Oncotarget 7, 27874-27888
14. Lundius, E. G., Stroth, N., Vukojevic, V., Terenius, L., and Svenningsson, P. (2013) Functional GPR37 trafficking protects against toxicity induced by 6-OHDA, MPP+ or rotenone in a catecholaminergic cell line. J Neurochem 124, 410-417
15. Robas, N., O'Reilly, M., Katugampola, S., and Fidock, M. (2003) Maximizing serendipity: strategies for identifying ligands for orphan G-protein-coupled receptors. *Curr Opin Pharmacol* 3, 121-126

16. Salon, J. A., Lodowski, D. T., and Palczewski, K. (2011) The significance of G protein-coupled receptor crystallography for drug discovery. *Pharmacol Rev* 63, 901-937

17. Dunham, J. H., Meyer, R. C., Garcia, E. L., and Hall, R. A. (2009) GPR37 surface expression enhancement via N-terminal truncation or protein-protein interactions. *Biochemistry* 48, 10286-10297

18. Kinsella, T. J., Vielhuber, K. A., Kunugi, K. A., Schupp, J., Davis, T. W., and Sands, H. (2000) Preclinical toxicity and efficacy study of a 14-day schedule of oral 5-iodo-2-pyrimidinone-2'-deoxyribose as a prodrug for 5-iodo-2'-deoxyuridine radiosensitization in U251 human glioblastoma xenografts. *Clin Cancer Res* 6, 1468-1475

19. Saif, M. W., Berk, G., Cheng, Y. C., and Kinsella, T. J. (2007) IPdR: a novel oral radiosensitizer. *Expert Opin Investig Drugs* 16, 1415-1424

20. Rautio, J., Kumpulainen, H., Heimbach, T., Oliyai, R., Oh, D., Jarvinen, T., and Savolainen, J. (2008) Prodrugs: design and clinical applications. *Nat Rev Drug Discov* 7, 255-270

21. Bundgaard, H. (1985) Design of Prodrugs. New York; Oxford: Elsevier

22. Chon, J., Stover, P. J., and Field, M. S. (2017) Targeting nuclear thymidylate biosynthesis. *Mol Aspects Med* 53, 48-56

23. Kubota, K., Niinuma, Y., Kaneko, M., Okuma, Y., Sugai, M., Omura, T., Uesugi, M., Uehara, T., Hosoi, T., and Nomura, Y. (2006) Suppressive effects of 4-phenylbutyrate on the aggregation of Pael receptors and endoplasmic reticulum stress. *J Neurochem* 97, 1259-1268

24. Vorbrüggen, H.; Ruh-Pohlenz C. (eds), Wiley, New York, (2001) Handbook of Nucleoside Synthesis 25. Bardos, T. (1982). U.S. Pat. No. 4,895,937

26. Schure, R.; Mar, A. A.; Pease, B.; Jones, W.; Felt, B.; Iyer, M. S. (1999) Improved Stereoselective Synthesis of the β-Anomer of 1-[3,5-Bis-O-(p-chlorobenzoyl)-2-deoxy-D-ribofuranosyl]-5-iodo-2-pyrimidinone. *Org. Process Res. Dev.*, 3, 135-138

27. Vorbrüggen, H.; C. Ruh-Pohlenz, L. A. Paquette Ed., Wiley, New York (2000) Organic Reactions, 55, p 100

28. ICH Harmonised Tripartite Guideline. Impurities: Guideline for Residual Solvents, Q3C (R5), 2011

29. Hoffer, M. (1960) a-Thymidin. *Chem. Ber.* 93, 2777-2781

30. Rolland, V.; Kotera, M.; Lhomme, J. (1997) Convenient Preparation of 2-Deoxy-3,5-di-O-p-toluoyl-α-D-erythro-pentofuranosyl Chloride. *Synth. Commun.*, 27, 3505-3511

31. Freskos, J. N. (1989) Synthesis of 2'-Deoxypyrimidine Nucleosides via Copper (I) Iodide Catalysis. *Nucleosides Nucleotides*, 8, 549-555

The invention claimed is:

1. A method for the treatment of parkinsonism, said method comprising administering to a patient in need thereof an effective amount of a compound having the general formula (III):

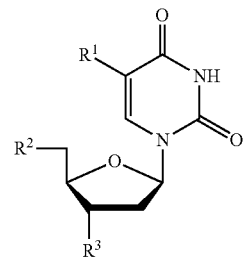

or a prodrug thereof, or a pharmaceutically acceptable salt or ester of said compound or prodrug, wherein $R^1$, $R^2$ and $R^3$ are independently (a) a halogen atom;
(b) a hydroxyl group;
(c) an amino group;
(d) a sulfhydryl group;
(e) a nitro group;
(f) an azido group;
(g) a cyano group;
(h) an ethenyl group;
(i) an ethynyl group;
(j) an aromatic/non-aromatic heterocyclic group;
(k) an aryl group,
   wherein (h), (i), (j) and (k) are optionally substituted with halogen, hydroxyl, nitro, azido, cyano, amino, sulfhydryl, phenyl, ethenyl, ethynyl, or an aromatic/non-aromatic heterocyclic group, and wherein the phenyl, ethenyl, ethynyl, or aromatic/non-aromatic heterocyclic group are optionally substituted with halogen, hydroxyl, nitro, azido, cyano, amino, or sulfhydryl;
(l) methyl substituted with halogen, hydroxyl, nitro, azido, cyano, amino, sulfhydryl, phenyl, ethenyl, ethynyl, or an aromatic/non-aromatic heterocyclic group, and wherein the phenyl, ethenyl, ethynyl, and aromatic/non-aromatic heterocyclic group are optionally substituted with halogen, hydroxyl, nitro, azido, cyano, amino, or sulfhydryl; or
(m) oxygen substituted with $C_1$-$C_{20}$ alkyl, $C_1$-$C_{20}$ acyl, $C_1$-$C_{20}$ alkoxycarbonyl, or carbamoyl.

2. The method according to claim 1, wherein $R^1$, $R^2$ and $R^3$ are independently (a) a halogen atom;
(b) a hydroxyl group;
(c) an amino group;
(d) an optionally substituted ethynyl group; or
(e) an optionally substituted phenyl group;
wherein (d) and (e) can be optionally substituted by a halogen atom, a hydroxyl group, or an amino group; or a prodrug of said compound, or a pharmaceutically acceptable salt or ester of said compound or prodrug.

3. The method according to claim 2, wherein $R^2$ and $R^3$ are hydroxyl groups; or a prodrug of said compound, or a pharmaceutically acceptable salt or ester of said compound or prodrug.

4. The method according to claim 3, wherein the compound is chosen from the group consisting of: 2'-deoxy-5-iodouridine, 2'-deoxy-5-(3-aminophenyl)-uridine, 2'-deoxy-5-ethynyluridine, and 2'-deoxy-5-hydroxyuridine, or a prodrug thereof, or a pharmaceutically acceptable salt or ester of said compound or prodrug.

5. The method according to claim 4, wherein the compound is 2'-deoxy-5-iodouridine (idoxuridine),

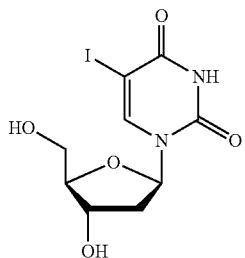 [SMILES: O=c1[nH]c(=O)n([C@H]2C[C@@H](O)[C@@H](CO)O2)cc1I]

or a prodrug thereof, or a pharmaceutically acceptable salt or ester of said compound or prodrug.

6. The method according to claim 5, wherein the prodrug is 1-((2R,4S,5R)-4-hydroxy-5-(hydroxymethyl)tetrahydrofuran-2-yl)-5-iodopyrimidin-2(1H)-one (ropidoxuridine); or 4-amino-1-((2R,4S,5R)-4-hydroxy-5-(hydroxymethyl)tetrahydrofuran-2-yl)-5-iodopyrimidin-2(1H)-one (5-iodo-2'-deoxycytidine).

7. The method according to claim 1, wherein the parkinsonism comprises one or more medical conditions chosen from the group consisting of Parkinson's disease (PD); dementia with Lewy bodies (DLB); multiple system atrophy (MSA); corticobasal degeneration (CBD); and progressive supranuclear palsy (PSP).

8. A method for the synthesis of 5-iodo-2-pyrimidinone-2'-deoxyribose (ropidoxuridine), comprising the steps:

(a) iodination of pyrimidin-2-ol, optionally as the hydrochloride salt, optionally using silver salt and iodine in a protic solvent to obtain 5-iodopyrimidin-2(1H)-one;

(b) reacting the 5-iodopyrimidin-2(1H)-one, or the tautomer thereof, with at least one trimethylsilyl (TMS) reagent to obtain 5-iodo-2-((trimethylsilyl)oxy)pyrimidine;

(c) coupling at least 2 equivalents of the 5-iodo-2-((trimethylsilyl)oxy)pyrimidine with a compound of the formula

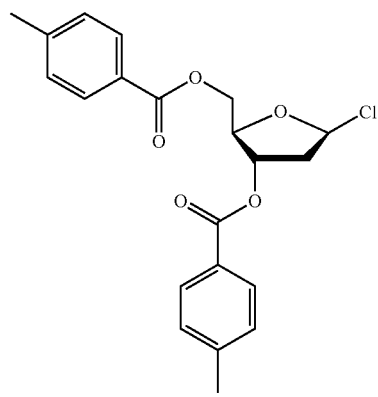 [SMILES: Cc1ccc(C(=O)OC[C@H]2O[C@@H](Cl)C[C@H]2OC(=O)c2ccc(C)cc2)cc1]

in chloroform, wherein the coupling is optionally performed in the presence of a copper salt;

(d) quenching the reaction mixture of step (c) with an alcohol, filtering the reaction mixture and evaporating the filtrate and purifying the residue to obtain protected ropidoxuridine; and (e) deprotecting the protected ropidoxuridine obtained in step (d) optionally using ammonia solution, an alkylamine, alkoxide, or carbonate to obtain ropidoxuridine.

9. The method according to claim 8, wherein said copper salt is copper(I)iodide.

10. The method according to claim 8, wherein the coupling in step (c) is performed without a copper salt.

11. The method according to claim 8, wherein the at least one trimethylsilyl (TMS) reagent is selected from the group consisting of hexamethyldisilizane (HMDS) and chlorotrimethylsilane (TMSCl).

12. The method according to claim 11, wherein the at least one trimethylsilyl (TMS) reagent is HMDS.

13. The method according to claim 11 wherein the at least one trimethylsilyl (TMS) reagent is a combination of HMDS and TMSCl.

14. The method according to claim 8, wherein step (b) is carried out in the presence of ammonium sulfate.

15. The method according to claim 8, wherein the alcohol in step (d) is methanol.

16. The method according to claim 8, wherein step (e) further comprises deprotecting the protected ropidoxuridine obtained in step (d) by adding sodium methoxide or potassium carbonate to a methanol or THF solution of the protected ropidoxuridine obtained in step (d).

17. The method according to claim 8, wherein step (e) further comprises deprotecting the protected ropidoxuridine obtained in step (d) by adding a solution of ammonia in methanol or alkylamine in methanol to the protected ropidoxuridine obtained in step (d).

* * * * *